(12) United States Patent
Hou et al.

(10) Patent No.: US 10,537,889 B2
(45) Date of Patent: Jan. 21, 2020

(54) ADDRESSABLE FLOW CELL USING PATTERNED ELECTRODES

(71) Applicant: Illumina, Inc., San Diego, CA (US)

(72) Inventors: Chenlu Hou, Belmont, CA (US); Byoungsok Jung, Atherton, CA (US); Yir-Shyuan Wu, Albany, CA (US); Tarun Khurana, Fremont, CA (US)

(73) Assignee: ILLUMINA, INC., San Diego, CA (US)

( * ) Notice: Subject to any disclaimer, the term of this patent is extended or adjusted under 35 U.S.C. 154(b) by 554 days.

(21) Appl. No.: 15/107,882

(22) PCT Filed: Dec. 30, 2014

(86) PCT No.: PCT/US2014/072699
§ 371 (c)(1),
(2) Date: Jun. 23, 2016

(87) PCT Pub. No.: WO2015/103225
PCT Pub. Date: Jul. 9, 2015

(65) Prior Publication Data
US 2016/0318016 A1 Nov. 3, 2016

Related U.S. Application Data

(60) Provisional application No. 61/922,604, filed on Dec. 31, 2013.

(51) Int. Cl.
*B01L 3/00* (2006.01)
*C40B 60/00* (2006.01)
*C12Q 1/6874* (2018.01)
*C12Q 1/68* (2018.01)

(52) U.S. Cl.
CPC ... *B01L 3/502715* (2013.01); *B01L 3/502761* (2013.01); *C12Q 1/6874* (2013.01); *B01L 2300/0636* (2013.01); *B01L 2400/0415* (2013.01)

(58) Field of Classification Search
CPC .................................. B01L 3/00; C12Q 1/68
See application file for complete search history.

(56) References Cited

U.S. PATENT DOCUMENTS

| | | | |
|---|---|---|---|
| 5,605,662 A | 2/1997 | Heller et al. | |
| 5,641,658 A | 6/1997 | Adams et al. | |
| 5,754,291 A | 5/1998 | Kain | |
| 5,981,956 A | 11/1999 | Stern | |
| 6,017,696 A | 1/2000 | Heller | |
| 6,172,218 B1 | 1/2001 | Brenner | |
| 6,210,891 B1 | 4/2001 | Nyren et al. | |
| 6,238,624 B1 | 5/2001 | Heller et al. | |
| 6,258,568 B1 | 7/2001 | Nyren | |
| 6,274,320 B1 | 8/2001 | Rothberg et al. | |
| 6,303,082 B1 | 10/2001 | John et al. | |
| 6,306,597 B1 | 10/2001 | Macevicz | |
| 6,403,367 B1 * | 6/2002 | Cheng | B01D 57/02 204/403.14 |
| 6,465,178 B2 | 10/2002 | Chappa et al. | |
| 6,969,488 B2 | 11/2005 | Bridgham et al. | |
| 7,057,026 B2 | 6/2006 | Barnes et al. | |
| 7,115,400 B1 | 10/2006 | Adessi et al. | |
| 7,172,864 B1 | 2/2007 | Heller et al. | |
| 7,314,542 B2 | 1/2008 | Smolko et al. | |
| 7,314,708 B1 | 1/2008 | Heller et al. | |
| 7,329,860 B2 | 2/2008 | Feng et al. | |
| 7,414,116 B2 | 8/2008 | Milton et al. | |
| 7,741,463 B2 | 6/2010 | Gormley et al. | |
| 7,985,656 B1 | 7/2011 | Mehta et al. | |
| 8,796,185 B2 * | 8/2014 | Kim | C40B 50/14 506/15 |
| 9,683,230 B2 | 6/2017 | Gormley et al. | |

(Continued)

FOREIGN PATENT DOCUMENTS

WO WO 1991/006678 5/1991
WO WO 1996/041011 12/1996
(Continued)

OTHER PUBLICATIONS

Margulies et al., Genome Sequencing in Microfabricated High-Density Picoliter Reactors, Nature, 2005, 437, 376-380. (Year: 2005).*
Margulies et al., Supplemental Methods, Genome Sequencing in Microfabricated High-Density Picoliter Reactors, Nature, 2005, 437, 1-34. (Year: 2005).*
Lei, K., Electrical Detection of Sandwich Immunoassay on Indium Tin Oxide Interdigitated Electrodes, Micro & Nano Letters, 2011, 6(3), 157-160. (Year: 2011).*
Sigma-Aldrich, Slides, Microscope Plain, USA Home, 2019, 1-2. (Year: 2019).*
Bentley, et al., "Accurate whole human genome sequencing using reversible terminator chemistry" *Nature* 456:53-59, 2008.
Braslavsky, et al., "Sequence information can be obtained from single DNA molecules" *PNAS* 100(7):3960-3964, 2003.

(Continued)

*Primary Examiner* — Amy M Bunker
(74) *Attorney, Agent, or Firm* — Illumina, Inc.

(57) ABSTRACT

Disclosed are methods and systems concerning flow cells for sequencing a nucleic acid sample that may be characterized by the following components: (a) a substrate having an inner surface facing a library sequencing region, and an outer surface; (b) a plurality of a plurality of forward and reverse amplification primers immobilized over the inner surface and providing a nucleic acid library capture surface of the library sequencing region; (c) a plurality of electrodes disposed along the inner surface directly under at least some of the forward and reverse amplification primers, and configured to provide, when charged, an electric field through the library capture surface and into the library sequencing region; (d) electrical leads connected to the plurality of electrodes to permit the electrodes to be independently addressable; and (e) fluidic couplings configured to deliver a plurality of nucleic acid libraries to the flow cell during different time periods.

11 Claims, 28 Drawing Sheets

(56) References Cited

U.S. PATENT DOCUMENTS

| | | |
|---|---|---|
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Ost et al. |
| 2007/0166705 A1 | 7/2007 | Milton et al. |
| 2008/0280773 A1 | 11/2008 | Fedurco et al. |
| 2009/0118128 A1 | 5/2009 | Liu et al. |
| 2009/0226975 A1 | 9/2009 | Sabot et al. |
| 2010/0137163 A1* | 6/2010 | Link ............... B01F 13/0071 506/16 |
| 2011/0027771 A1 | 2/2011 | Deng et al. |
| 2011/0059865 A1 | 3/2011 | Smith et al. |
| 2012/0040853 A1* | 2/2012 | Pierik ................ C12Q 1/6851 506/9 |
| 2012/0252682 A1 | 10/2012 | Zhou et al. |
| 2012/0270740 A1* | 10/2012 | Edwards ............ C12Q 1/6874 506/2 |
| 2013/0034880 A1 | 2/2013 | Oldham |

FOREIGN PATENT DOCUMENTS

| | | |
|---|---|---|
| WO | WO 1998/044151 | 10/1998 |
| WO | WO 2000/006770 | 2/2000 |
| WO | WO 2000/018957 | 4/2000 |
| WO | 2000/037163 | 6/2000 |
| WO | WO 2000/031148 | 6/2000 |
| WO | WO 2000/053812 | 9/2000 |
| WO | WO 2001/001143 | 1/2001 |
| WO | 2001/032930 | 5/2001 |
| WO | WO 2002/012566 | 2/2002 |
| WO | WO 2002/046456 | 6/2002 |
| WO | WO 2002/072892 | 9/2002 |
| WO | WO 2003/014392 | 2/2003 |
| WO | WO 2004/018493 | 3/2004 |
| WO | WO 2004/018497 | 3/2004 |
| WO | WO 2004/069849 | 8/2004 |
| WO | WO 2005/024010 | 3/2005 |
| WO | WO 2005/065814 | 7/2005 |
| WO | 2006/065598 | 6/2006 |
| WO | WO 2006/064199 | 6/2006 |
| WO | WO 2006/120433 | 11/2006 |
| WO | WO 2007/010251 | 1/2007 |
| WO | WO 2007/123744 | 11/2007 |
| WO | WO 2013/063382 | 5/2013 |
| WO | 2013/096819 | 6/2013 |
| WO | WO 2015/103225 | 7/2015 |

OTHER PUBLICATIONS

Brenner, et al., "Gene expression analysis by massively parallel signature sequencing (MPSS) on microbead arrays" *Nature Biotechnology* 18:630-634, 2000.

Margulies, et al., "Genome sequencing in microfabricated high-density picolitre reactors" *Nature* 437:376-380, 2005.

Ronaghi, et al., "Real-time DNA sequencing using detection of pyrophosphate release." *Analytical Biochemistry* 242(1):84-89, 1996.

Ronaghi, et al., "A sequencing method based on real-time pyrophosphate." *Science* 281(5375):363, 1998.

Ronaghi, M. "Pyrosequencing sheds light on DNA sequencing." *Genome Research* 11(1):3-11, 2001.

Shendure, et al., "Accurate Multiplex Polony Sequencing of an Evolved Bacterial Genome" *Science* 309:1728-1732, 2005.

PCT International Search Report and Written Opinion dated Apr. 14, 2015 issued in PCT/US2014/072699.

PCT International Preliminary Report on Patentability dated Jul. 14, 2016 issued in PCT/US2014/072699.

* cited by examiner

Planar view

Side view

ADDRESSABLE FLOW CELL USING PATTERNED ELECTRODES

CROSS-REFERENCE TO RELATED APPLICATIONS

This application claims the benefit of and priority to U.S. Provisional Application Ser. No. 61/922,604, filed Dec. 31, 2013, the contents of which are incorporated herein by reference in their entirety and for all purposes.

INCORPORATION BY REFERENCE

All documents cited are, in relevant part, incorporated herein by reference in their entireties for the purposes indicated by the context of their citation herein. However, the citation of any document is not to be construed as an admission that it is prior art with respect to the present disclosure.

BACKGROUND

The study of biology has recently benefited from improved methods of analysis and sequencing of nucleic acids. While the "human genome" has been sequenced there are still vast amounts of genomic material to analyze, e.g., genetic variation between different individuals, tissues, additional species, etc.

Devices for DNA sequencing based on separation of fragments of differing length were first developed in the 1980s, and have been commercially available for a number of years. A number of new DNA sequencing technologies are based on the massively parallel analysis of unamplified (WO00006770; Proceedings of the National Academy of Sciences U.S.A, 100, 3960-3964 (2003)) or amplified single molecules, either in the form of planar arrays (WO9844151) or on beads (WO04069849; Nature, 437, 376-380 (2005); Science, 309, 5741, 1728-1732 (2005); Nat Biotechnol. 6, 630-6344 (2000)).

The methodology used to analyze the sequence of the nucleic acids in such new sequencing techniques is often based on the detection of fluorescent nucleotides or oligonucleotides. The detection instrumentation used to read the fluorescence signals on such arrays may be based on either epifluorescence or total internal reflection microscopy, for example as described in WO9641011, WO00006770 or WO02072892.

Multiplexing enables large sample numbers to be simultaneously sequenced during a single experiment. Some methodologies utilize individual "barcode" sequences that are added to each sample so that they may be differentiated during data analysis.

SUMMARY

Certain disclosed embodiments concern flow cells for sequencing a nucleic acid sample that may be characterized by the following components: (a) a substrate having an inner surface facing a library sequencing region, and an outer surface; (b) a plurality of a plurality of forward and reverse amplification primers immobilized over the inner surface and providing a nucleic acid library capture surface of the library sequencing region; (c) a plurality of electrodes disposed along the inner surface directly under at least some of the forward and reverse amplification primers, and configured to provide, when charged, an electric field through the library capture surface and into the library sequencing region; (d) electrical leads connected to the plurality of electrodes to permit the electrodes to be independently addressable; and (e) fluidic couplings configured to deliver a plurality of nucleic acid libraries to the flow cell during different time periods.

In some implementations, the flow cell further includes one or more separation structures disposed over the inner surface and defining multiple substantially parallel lanes on the library sequencing region. In some implementations, the fluidic couplings are configured deliver the nucleic acid libraries to distinct lanes.

In some implementations, the flow cell further includes a cover arranged substantially parallel to and spaced apart from the inner surface of the substrate, wherein the cover defines a boundary of the library sequencing region. In some implementations, the cover is substantially transmissive to radiation of wavelengths suitable for imaging.

In some implementations, the cover includes a film of transparent electrically conductive film attached to an electrical lead.

In some implementations, the library capture surface of the attachment layer occupies an area of between about 60 $mm^2$ and about 2400 $mm^2$.

In some implementations, the density of the plurality of forward and reverse amplification primers attached to the attachment layer is at least 1 fmol per $mm^2$. In some implementations, the density of the hybridized polynucleotides attached to the solid support is $10,000/mm^2$ to $2,000,000/mm^2$.

In some implementations, the flow cell further includes an attachment layer to which the plurality of forward and reverse amplification primers is attached.

In some implementations, the controller is designed or programmed to apply the positive charge to the first electrode at a voltage in the range of approximately 0.5-3V. In some implementations, the controller is designed or programmed to apply the positive charge to the second electrode at a voltage in the range of approximately 0.5-3V. In some implementations, the controller is designed or programmed to apply the positive charge to the first electrode to produce a current in the range of approximately 250 nA-5 µA. In some implementations, the controller is designed or programmed to apply the positive charge to the second electrode to produce a current in the range of approximately 250 nA-5 µA. In some implementations, the controller is designed or programmed to apply the positive charge to the first electrode to produce an electric field in the range of approximately 10-200 V/cm. In some implementations, the controller is designed or programmed to apply the positive charge to the second electrode to produce an electric field in the range of approximately 10-200 V/cm. In some implementations, the controller is designed or programmed to operate the first and second electrodes in direct current (DC) mode. In some implementations, the controller is designed or programmed to apply the positive charge to the second electrode using direct current (DC).

In some implementations, the electrodes are disposed perpendicular to the length of the solid support. In some implementations, the electrodes are disposed in an array. In some implementations, the plurality of electrodes includes about 2-12 electrodes disposed along the solid support. In some implementations, each of the plurality of electrodes has a surface area of approximately 100 $um^2$ to 200 $mm^2$. In some implementations, each of the plurality of electrodes is substantially round-shaped. In some implementations, the electrodes are made of gold.

In some implementations, the plurality of electrodes are made of indium-doped tin oxide (ITO). In other implementations, the plurality of electrodes are made of a conductor selected from the group consisting of silver, tin, titanium, copper, platinum, palladium, polysilicon, and carbon. In some implementations, the conductance of each of the plurality of electrodes is in the range of approximately 280 nS-1 µS.

In some implementations, the flow cell further includes a controller designed or programmed to deliver electrical charge to each of the electrodes independently. In some implementations, the controller is further designed or programmed to deliver a positive charge to one electrode while delivering negative charge to a plurality of adjacent electrodes. In some implementations, the controller is further designed or programmed to control delivery of the different nucleic acid libraries to the flow cell at times corresponding to delivery of positive charge to different electrodes.

In some implementations, the forward and reverse amplification primers are configured to hybridize to specific gene sequences of the nucleic acid libraries. In some implementations, the specific gene sequences are one of: a barcode region of the nucleic acid libraries, an adapter region of the nucleic acid libraries, and nucleic acid sequences of interest within the nucleic acid libraries.

In some implementations, amplification primers configured to hybridize to a first gene sequence are localized in a first region of the flow cell, and wherein amplification primers configured to hybridize to a second gene sequence are localized to a second, spatially separate, region of the flow cell. In some implementations, the amplification primers are localized to the first and second regions using electric fields generated by the plurality of electrodes. In some implementations, the amplification primers are disposed on one or more beads immobilized on the inner surface of the substrate. In some implementations, the amplification primers are disposed on one or more beads immobilized in one or more wells of the inner surface of the substrate.

Certain disclosed embodiments concern methods of sequencing nucleic acid samples that may be characterized by the following operations: (a) introducing a first nucleic acid library to a library sequencing region of a flow cell including: a substrate having an inner surface facing the library sequencing region, and an outer surface, a plurality of forward and reverse amplification primers disposed over the inner surface and providing a nucleic acid library capture surface of the library sequencing region, and a plurality of electrodes disposed along the substrate proximate the library capture surface; (b) applying a positive charge to a first set of one or more electrodes, from the plurality of electrodes, while the first nucleic acid library flows through the library sequencing region to thereby attract nucleic acids from the first nucleic acid library to the forward and reverse amplification primers disposed proximate the first set of one or more electrodes such that members of the first nucleic acid library hybridize to forward and reverse amplification primers proximate the first set of one or more electrodes, wherein members of the first nucleic acid library do not substantially hybridize to forward and reverse amplification primers located proximate electrodes that do not have positive charge applied; (c) introducing a second nucleic acid library to a library sequencing region flow cell; and (d) applying a positive charge to a second set of one or more electrodes, from the plurality of electrodes, while the second nucleic acid library flows through the library sequencing region to thereby attract nucleic acids from the second nucleic acid library to the forward and reverse amplification primers disposed proximate the second set of one or more electrodes such that members of the second nucleic acid library hybridize to forward and reverse amplification primers proximate the second set of one or more electrodes, wherein members of the second nucleic acid library do not substantially hybridize to forward and reverse amplification primers located proximate electrodes that do not have positive charge applied.

In some implementations, introducing the first nucleic acid library and introducing the second nucleic acid library includes introducing the first and second nucleic acid libraries to the same lane of the flow cell.

In some implementations, the method further includes applying negative charge to electrodes adjacent to the first electrode while applying the positive charge to the first electrode.

In some implementations, the method further includes (e) introducing a third nucleic acid library to a library sequencing region flow cell and (f) applying a positive charge to a third set of one or more electrodes, from the plurality of electrodes, while the third nucleic acid library flows through the library sequencing region to thereby attract nucleic acids from the third nucleic acid library to the forward and reverse amplification primers disposed proximate the third set of one or more electrodes such that members of the third nucleic acid library hybridize to forward and reverse amplification primers proximate the third set of one or more electrodes, wherein members of the third nucleic acid library do not substantially hybridize to forward and reverse amplification primers located proximate electrodes that do not have positive charge applied.

In some implementations, the method further includes, when applying a positive charge to a first electrode, applying a positive charge to third electrode from among the plurality of electrodes, which third electrode is not the second electrode, such that members of the first nucleic acid library hybridize to forward and reverse amplification primers proximate the other electrode.

In some implementations, introducing the first nucleic acid library includes flowing the first nucleic acid library in a solution including one or more protective reagents that blocks detrimental effects of water electrolysis.

In some implementations, the one or more protective reagents undergoes a redox reaction at an electric potential that is below the electric potential at which water electrolyzes, and wherein the redox reaction produces only products that are substantially benign to nucleic acids. In some implementations, the one or more protective reagents is selected from the group consisting of α-thioglycerol, dithiothreitol, hydroquinone, ferrocyanide, and β-mercaptoethanol. In some implementations, the one or more protective reagents is present in the solution at a concentration of about 25 mM-1.5 M.

In some implementations, the method further includes preparing the first nucleic acid library by: fragmenting a complex polynucleotide sample to generate a plurality of target polynucleotide fragments; and ligating identical mismatched adapter polynucleotides to both ends of each of the different target polynucleotide fragments to form adapter-target constructs, wherein each mismatched adapter is formed from two annealed polynucleotide strands that form a bimolecular complex including at least one double-stranded region and a mismatched region including portions of both strands, wherein the ligating covalently attaches each strand of the at least one double-stranded region to each respective strand of each of the different target polynucleotide fragment to generate adapter-target constructs including covalently attached 5' and 3' adapter sequences.

In some implementations, each hybridized nucleic acid is amplified by: forming at least one nucleic acid template including the at least one nucleic acid to be amplified, wherein the at least one nucleic acid contains an oligonucleotide sequence Y at the 5' end and an oligonucleotide sequence Z at the 3' end, and the at least one nucleic acid carries a means for immobilizing the at least one nucleic acid to a solid support at the 5' end; mixing the at least one nucleic acid template, in the presence of the solid support, with one or more colony primers X, each of which can hybridize to the oligonucleotide sequence Z and carries a means for immobilizing the colony primer to the solid support at the 5' end, whereby the 5' ends of both the at least one nucleic acid template and the colony primers are immobilized to the solid support, wherein the 5' ends of both the at least one nucleic acid template and the colony primers are immobilized to the solid support such that they cannot be removed by washing with water or aqueous buffer under DNA denaturing conditions; and performing one or more nucleic acid amplification reactions on the immobilized nucleic acid template, so that nucleic acid colonies are generated.

In some implementations, the method further includes: moving one or more fluorescently labeled reagents through the flow cell into contact with the hybridized members of the first and second nucleic acid libraries, wherein the reagents include components to extend a second sequence complementary to the hybridized polynucleotides; illuminating the hybridized polynucleotides with at least one excitation laser coupled through a fiberoptic device; detecting, using at least one charge-coupled device (CCD) camera, fluorescence emissions of the fluorescently labeled reagents; and determining, based on the fluorescence emissions, an identity of the second sequence.

In some implementations, the forward and reverse amplification primers are configured to hybridize to specific gene sequences of the nucleic acid libraries. In some implementations, the specific gene sequences are one of: a barcode region of the nucleic acid libraries, an adapter region of the nucleic acid libraries, and nucleic acid sequences of interest within the nucleic acid libraries. In some implementations, amplification primers configured to hybridize to a first gene sequence are localized in a first region of the flow cell, and wherein amplification primers configured to hybridize to a second gene sequence are localized to a second, spatially separate, region of the flow cell. In some implementations, the amplification primers are localized to the first and second regions using electric fields generated by the plurality of electrodes. In some implementations, the amplification primers are disposed on one or more beads immobilized on the inner surface of the substrate. In some implementations, the amplification primers are disposed on one or more beads immobilized in one or more wells of the inner surface of the substrate.

Certain disclosed embodiments concern systems for sequencing polynucleotide samples that may be characterized by the following components: (a) a solid support having a plurality of electrodes disposed thereon, the solid support including an attachment layer over the plurality of electrodes, the attachment layer having a library capture surface including a plurality of forward and reverse amplification primers immobilized thereon; (b) electrical leads connected to the plurality of electrodes to permit the electrodes to be independently addressable; (c) a fluid direction system for controllably delivering a plurality of polynucleotide libraries in a buffer with a reducing agent to the library capture surface during different time periods; and (d) a controller for controlling the fluid direction system and for delivering current and/or potential to the electrodes, wherein the controller is designed or programmed to apply a positive charge to a first electrode of the plurality of electrodes while the fluid direction system delivers a first polynucleotide library along the solid support such that polynucleotides from the first polynucleotide library are attracted to forward and reverse amplification primers disposed proximate the first electrode such that members of the first polynucleotide library hybridize to forward and reverse amplification primers proximate the first electrode, wherein members of the first polynucleotide library do not substantially hybridize to forward and reverse amplification primers located proximate electrodes that do not have positive charge applied, and apply a positive charge to a second electrode of the plurality of electrodes while the fluid direction system delivers a second polynucleotide library along the solid support such that polynucleotides from the second polynucleotide library are attracted to forward and reverse amplification primers disposed proximate the second electrode such that members of the second polynucleotide library hybridize to forward and reverse amplification primers proximate the second electrode, wherein members of the second polynucleotide library do not substantially hybridize to forward and reverse amplification primers located proximate electrodes that do not have positive charge applied.

In some implementations, the solid support is provided in a flow cell including one or more fluidic channels in which the forward and reverse amplification primers are attached, the one or more fluidic channels defining multiple substantially parallel lanes on the library capture surface. In some implementations, the controller is further designed or programmed to cause the fluid direction system to deliver the polynucleotide libraries to distinct lanes of the flow cell.

In some implementations, the system further includes a cover substantially parallel to the solid support and spaced apart from the inner surface, wherein the cover defines a boundary of the library capture surface. In some implementations, the cover is substantially transmissive to radiation of wavelengths suitable for imaging. In some implementations, the cover includes a transparent electrically conductive layer attached to an electrical lead.

In some implementations, the conductive layer includes indium-doped tin oxide (ITO).

In some implementations, the library capture surface of the attachment layer occupies an area of between about 60 $mm^2$ and about 2400 $mm^2$.

In some implementations, the density of the plurality of forward and reverse amplification primers attached to the attachment layer is at least 1 fmol per $mm^2$. In some implementations, the density of the hybridized polynucleotides attached to the solid support is 10,000/$mm^2$ to 2,000,000/$mm^2$. In some implementations, the system further includes an attachment layer to which the plurality of forward and reverse amplification primers are attached.

In some implementations, the controller is designed or programmed to apply the positive charge to the first electrode at a voltage in the range of approximately 0.5-3V. In some implementations, the controller is designed or programmed to apply the positive charge to the second electrode at a voltage in the range of approximately 0.5-3V. In some implementations, the controller is designed or programmed to apply the positive charge to the first electrode to produce a current in the range of approximately 250 nA-5 µA. In some implementations, the controller is designed or programmed to apply the positive charge to the second electrode to produce a current in the range of approximately 250 nA-5 µA. In some implementations, the controller is designed or programmed to apply the positive charge to the first electrode to produce an electric field in the range of approximately 10-200 V/cm. In some implementations, the controller is designed or programmed to apply the positive charge to the second electrode to produce an electric field in the range of approximately 10-200 V/cm. In some implementations, the controller is designed or programmed to operate the first and second electrodes in direct current (DC) mode. In some implementations, the controller is designed or programmed to apply the positive charge to the second electrode using direct current (DC).

In some implementations, the electrodes are disposed perpendicular to the length of the solid support. In some implementations, the electrodes are disposed in an array. In some implementations, the plurality of electrodes includes about 2-12 electrodes are disposed along the solid support. In some implementations, each of the plurality of electrodes has a surface area of approximately 100 um$^2$ to 200 mm$^2$. In some implementations, each of the plurality of electrodes is substantially round-shaped. In some implementations, the electrodes are made of gold. In other implementations, the plurality of electrodes is made of indium-doped tin oxide (ITO). In other implementations, the plurality of electrodes is made of a conductor selected from the group consisting of silver, tin, titanium, copper, platinum, palladium, polysilicon, and carbon. In some implementations, the conductance of each of the plurality of electrodes is in the range of approximately 280 nS-1 µS.

In some implementations, the controller is further designed or programmed to deliver a positive charge to one electrode while delivering negative charge to a plurality of adjacent electrodes. In some implementations, the controller is further designed or programmed to control delivery of the different nucleic acid libraries to the flow cell at times corresponding to delivery of positive charge to different electrodes.

In some implementations, the forward and reverse amplification primers are configured to hybridize to specific gene sequences of the polynucleotide libraries. In some implementations, the specific gene sequences are one of: a barcode region of the polynucleotide libraries, an adapter region of the polynucleotide libraries, and polynucleotide sequences of interest within the polynucleotide libraries. In some implementations, amplification primers configured to hybridize to a first gene sequence are localized in a first region of the flow cell, and wherein amplification primers configured to hybridize to a second gene sequence are localized to a second, spatially separate, region of the flow cell. In some implementations, the amplification primers are localized to the first and second regions using electric fields generated by the plurality of electrodes. In some implementations, the amplification primers are disposed on one or more beads immobilized on the library capture surface. In some implementations, the amplification primers are disposed on one or more beads immobilized in one or more wells of the library capture surface.

DETAILED DESCRIPTION

Definitions

Figure 1A:
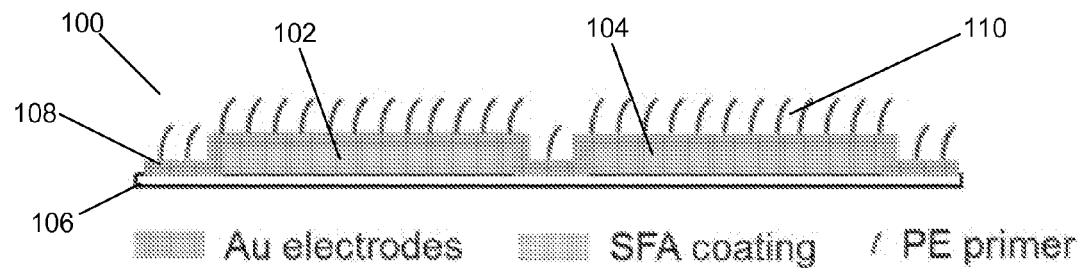
FIG. 1A shows a portion of a flow cell including two electrodes disposed on a solid support and an attachment layer, in accordance with some implementations.

Before describing some of the embodiments in detail, it is to be understood that the invention herein is not limited to use with any particular nucleic acids or biological systems. It is also to be understood that the terminology used herein is for the purpose of describing particular embodiments only, and is not intended to be limiting. As used in this specification and the appended claims, the singular forms "a," "an," and "the" include plural referents unless the context clearly dictates otherwise. Thus, for example, reference to "a flow cell" optionally includes a combination of two or more flow cells, and the like.

As used herein, the terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA and DNA molecules. The term "polynucleotide" includes, without limitation, single- and double-stranded polynucleotide. The terms should be understood to include, as equivalents, analogs of either DNA or RNA made from nucleotide analogs. The terms as used herein also encompass cDNA, that is complementary, or copy, DNA produced from an RNA template, for example by the action of reverse transcriptase. The terms nucleic acid, polynucleotide and oligonucleotide are not intended to denote any particular difference in size, sequence, or other property unless specifically indicated otherwise. For clarity of description the terms may be used to distinguish one species of molecule from another when describing a particular method or composition that includes several molecular species.

The single stranded polynucleotide molecules sequenced by the systems and devices herein can have originated in single-stranded form, as DNA or RNA or have originated in double-stranded DNA (dsDNA) form (e.g. genomic DNA fragments, PCR and amplification products and the like). Thus a single stranded polynucleotide may be the sense or antisense strand of a polynucleotide duplex. Methods of preparation of single stranded polynucleotide molecules suitable for use in the described methods using standard techniques are well known in the art. The precise sequence of the primary polynucleotide molecules is generally not material to the disclosed embodiments and may be known or unknown. The single stranded polynucleotide molecules can represent genomic DNA molecules (e.g., human genomic DNA) including both intron and exon sequences (coding sequence), as well as non-coding regulatory sequences such as promoter and enhancer sequences.

In certain embodiments, a nucleic acid contains a "target" region that it is desired to fully or partially sequence. The nature of the target region is not limiting to the disclosed embodiments. It may be of a previously known or unknown sequence and may be derived, for example, from a genomic DNA fragment, a cDNA, etc. The nucleic acid molecule may also include non-target sequences, for example at the 5' and 3' ends flanking the target region. If the nucleic acid is formed by solid-phase nucleic acid amplification, these non-target sequences may be derived from the primers used for the amplification reaction. Sites for cleavage of one or both strands of a double-stranded nucleic acid may be positioned in the non-target sequences.

The nucleic acid may form part of a cluster or colony comprised of many such nucleic acid molecules, and the cluster or colony may itself form part of an array of such clusters or colonies, referred to herein as a "clustered array". On such an array each nucleic acid molecule within each colony will comprise the same target region, whereas different colonies may be formed of nucleic acid molecules comprising different target regions. In certain embodiments, at least 90%, more preferably at least 95%, of the colonies on a given clustered array will be formed from nucleic acid molecules comprising different target regions, although within each individual colony on the array all nucleic acid molecules will contain the same target region.

As used throughout, the term "target nucleic acid" can be any molecule to be selected and, optionally, amplified or sequenced. Target nucleic acids for use in the provided methods may be obtained from any biological sample using known, routine methods. Suitable biological samples include, but are not limited to, a blood sample, biopsy specimen, tissue explant, organ culture, biological fluid or any other tissue or cell preparation, or fraction or derivative thereof or isolated therefrom. The biological sample can be a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. For example, polynucleotide molecules may be obtained from primary cells, cell lines, freshly isolated cells or tissues, frozen cells or tissues, paraffin embedded cells or tissues, fixed cells or tissues, and/or laser dissected cells or tissues. Biological samples can be obtained from any subject or biological source including, for example, human or non-human animals, including mammals and non-mammals, vertebrates and invertebrates, and may also be any multi-cellular organism or single-celled organism such as a eukaryotic (including plants and algae) or prokaryotic organism, archaeon, microorganisms (e.g. bacteria, archaea, fungi, protists, viruses), and aquatic plankton.

The target nucleic acid described herein can be of any length suitable for use in the provided methods. For example, the target nucleic acids can be at least 10, at least 20, at least 30, at least 40, at least 50, at least 75, at least 100, at least 150, at least 200, at least 250, at least 500, or at least 1000 nucleotides in length or longer. Generally, if the target nucleic acid is a small RNA molecule, the target nucleic acid will be at least 10 nucleotides in length. Thus, the target nucleic acid sequences can comprise RNA molecules, for example, small RNA molecules including, but not limited to miRNA molecules, siRNA molecules, tRNA molecules, rRNA molecules, and combinations thereof. In some embodiments, the target nucleic acid sequence comprises single-stranded DNA.

In certain embodiments, the nucleic acid to be sequenced through use of the disclosed embodiments is immobilized upon a substrate (e.g., a substrate within a flow cell or one or more beads upon a substrate such as a flow cell, etc.). The term "immobilized" or "attached" as used herein is intended to encompass direct or indirect, covalent or non-covalent attachment, unless indicated otherwise, either explicitly or by context. In certain embodiments, covalent attachment may be used, but generally all that is required is that the molecules (for example, nucleic acids) remain immobilized or attached to a support under conditions in which it is intended to use the support, for example in applications requiring nucleic acid amplification and/or sequencing. Typically oligonucleotides to be used as capture oligonucleotides or amplification oligonucleotides are immobilized such that a 3' end is available for enzymatic extension and at least a portion of the sequence is capable of hybridizing to a complementary sequence. Immobilization can occur via hybridization to a surface attached oligonucleotide, in which case the immobilized oligonucleotide or polynucleotide may be in the 3'-5' orientation. Alternatively, immobilization can occur by means other than base-pairing hybridization, such as the covalent attachment set forth above.

The term "library" refers to a collection or plurality of nucleic acid template molecules which have a common use or common property such as a common origin; e.g., all members of the library come from a single sample. The members of the library may be processed or modified to so that their membership in the library is clearly identified. For example, all members of a library may share a common sequence at their 5' ends and a common sequence at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates be related in terms of sequence and/or source.

As used throughout, "primers" and "amplification primers" are used interchangeably and are oligonucleotide sequences that are capable of annealing specifically to a polynucleotide sequence to be amplified under conditions encountered in a primer annealing step of an amplification reaction.

The term "solid support" (or "substrate" in certain usages) as used herein refers to any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. In many embodiments, the solid support is a glass surface (e.g., the planar surface of a flow cell channel). The solid support may be mounted on the interior of a flow cell to allow the interaction with solutions of various reagents. In certain embodiments the solid support may comprise an inert substrate or matrix which has been "functionalized," for example by the application of a layer or coating of an intermediate material comprising reactive groups which permit covalent attachment to molecules such as polynucleotides. By way of non-limiting example such supports can include polyacrylamide hydrogels supported on an inert substrate such as glass. In such embodiments the molecules (polynucleotides) can be directly covalently attached to the intermediate material (e.g. the hydrogel) but the intermediate material can itself be non-covalently attached to the substrate or matrix (e.g. the glass substrate). Covalent attachment to a solid support is to be interpreted accordingly as encompassing this type of arrangement. In certain embodiments, a solid support may contain a nucleic acid library capture surface having moieties for immobilizing target nucleic acids that come in contact with the substrate. The moieties may be a plurality of primers or other capture moieties immobilized on a support surface. In one example, the primers are forward and reverse amplification primers.

As used herein, the term "interrogate" can refer to any interaction of a molecule on the array with any other chemical or molecule and may also refer to any analysis of a detectable signal from a molecule on the array or any other molecule which is bound thereto or associated therewith. In one embodiment "interrogation" encompasses a target polynucleotide on the array functioning as a template upon which DNA polymerase acts. In other words, "interrogating" can encompass contacting the target polynucleotides with another molecule, e.g., a polymerase, a nucleoside triphosphate, a complementary nucleic acid sequence, where the physical interaction provides information regarding a characteristic of the arrayed target polynucleotide. The contacting can involve covalent or non-covalent interactions with the other molecule. As used herein, "information regarding a characteristic" means information about the identity or sequence of one or more nucleotides in the target polynucleotide, the length of the polynucleotide, the base composition of the polynucleotide, the $T_m$ of the polynucleotide, the presence of a specific binding site for a polypeptide, a complementary nucleic acid or other molecule, the presence of an adduct or modified nucleotide, or the three-dimensional structure of the polynucleotide.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 30 bp) that can be used to identify a larger sequence or region, e.g. that can be aligned and specifically assigned to a chromosome or genomic region or gene.

As used herein, the terms "aligned", "alignment", or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina® Genomics Analysis® pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at www.ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. Such sequences may be referred to as chromosome reference sequences. Other examples of reference sequences include genomes of other species, as well as chromosomes, sub-chromosomal regions (such as strands), etc. of any species. In various embodiments, the reference sequence is a consensus sequence or other combination derived from multiple individuals. However, in certain applications, the reference sequence may be taken from a particular individual.

Introduction

The disclosed embodiments pertain to systems and devices to analyze a large number of different nucleic acid sequences from, e.g., clonally amplified single-molecule DNA arrays in flow cells, or arrays of immobilized beads. In particular, the systems and devices utilize electrode arrays configured to selectively capture and isolate specific nucleic acids on regions of a solid support. In various disclosed embodiments, the electrode arrays spatially isolate nucleic acid libraries, so that one or more libraries are immobilized at one location on a library capture surface while other libraries are immobilized at one or more other locations on the library capture surface. The members of a nucleic acid library are captured on a region proximate an electrode when a positive bias is selectively applied to the electrode. By bringing different libraries to the library capture surface at different times, when different electrodes are activated by applying a positive charge, the system spatially isolates the nucleic acid libraries from one another. In some implementations, different libraries (possibly from different samples) are captured at different regions of a flow cell for multiplexed sequencing. The regions are associated with specific libraries. The nucleic acids in the different regions are sequenced in parallel but are identified by their libraries which are associated with distinct regions, which have discrete electrodes.

The electrodes may be attached to or proximate a solid support having a library capture surface. The electrodes are independently addressable, such that one or more selected electrodes are given a positive charge while the remaining electrodes are given a negative or neutral charge. In this manner, a system may apply a spatially isolated electric field to a library capture surface and thereby selectively capture and spatially isolate a library on a region of the solid support. A spatially and temporally controlled electric field applied in this manner may be used in various sequencing platforms to increase sequencing throughput and sensitivity. Specifically, an addressable electric field can isolate different nucleic samples into different regions of a solid support such as a support used in sequencing flow cells or chips for multiplexed sequencing.

In some cases, an electric field may be employed to deliver forward-read primers and reverse-read primers to different regions of the sequencing flow cells or chips for paired-end read in parallel, in which a forward read is performed on polynucleotides hybridized to the forward-read primers and a reverse read is performed on polynucleotides hybridized to the reverse-read primers.

In some embodiments, the primers recognize an adapter region of the target library polynucleotides. In other embodiments, primers designed for gene or other sequence-specific capture may recognize specific sequences of the target polynucleotides. Alternatively, the primers may recognize a barcode region of the target polynucleotides. In some embodiments, an electric field may be used to localize different sequence-specific capture primers in specific regions of a flow cell, followed by hybridization of target polynucleotide libraries with or without an electric field.

In certain DNA sequencing technologies that utilize beads containing polynucleotide libraries located in different regions of a chip for multiplexed sequencing, an electric field may be used to distribute those beads to their targeted locations. In some embodiments, the beads may be functionalized with primers and may be immobilized on flow cell surface or wells or one or more electrodes, such that an electric field may direct hybridization onto the immobilized beads.

In technologies that isolate polynucleotide templates in sensor wells for sequencing, an electric field may deliver forward-read and reverse-read primers into different sensor wells so that the forward and reverse reads may be performed in parallel, reducing the amount of time required for paired-end sequencing. In technologies that isolate single-stranded DNA templates in zero-mode waveguides on a chip, an electric field may be used to distribute DNA libraries from different samples to different regions of the chip for multiplexed sequencing.

The various methods, apparatus, systems and uses are described in further detail in the following examples which are not in any way intended to limit the scope of the disclosure. Many of the embodiments pertain to sequencing by synthesis technology that generates clusters from sample DNA captured by paired end primers on a solid support. Those of skill in the art will understand that numerous other sequencing technologies may profit from electric field capture of nucleic acids at discrete locations on a flow cell or other sequencing device. The attached Figures are meant to be considered as integral parts of the specification and description of the invention. The following examples are offered to illustrate, but not to limit the disclosure.

Preparation of Library Capture Surface of the Flow Cell

In the embodiment depicted in FIG. 1A, the displayed portion of a flow cell 100 includes two electrodes 102, 104 disposed on a solid support 106 and an attachment layer 108. In this example, a silane-free acrylamide (SFA) coating serves as the attachment layer 108. Amplification primers 110 are immobilized in the attachment layer 108. In this embodiment, paired-end (PE) primers serve as the amplification primers 110. The electrodes 102, 104 in the embodiment of FIG. 1A are made of gold.

Figure 1B:
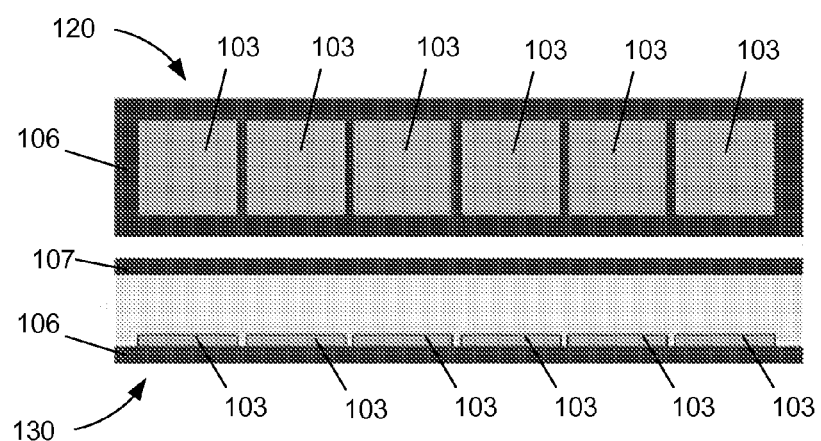
FIG. 1B shows a top and side view of a lane of a flow cell including six electrodes disposed on the flow cell, in accordance with some implementations.

FIG. 1B presents a top view 120 and a side view 130 of a library capture surface such as a lane of a flow cell such as cell 100 from FIG. 1A. In both views, six electrodes 103 are disposed in a row down the lane of the flow cell on support 106 (attachment layer not depicted). A top plate 107 defines an upper surface of the flow cell. The electrodes are connected to electrical leads that can independently deliver a positive or negative charge to each electrode. A flow cell may include any number of lanes as can fit on the flow cell. In certain embodiments, a flow cell includes 6-12 lanes.

Library Preparation

In some embodiments, the DNA to be sequenced is fragmented to a designated optimal length. Because DNA fragmentation does not result in homogeneous, blunt-ended fragments, end repair may be performed to ensure that each molecule is free of overhangs, and contains 5' phosphate and 3' hydroxyl groups. Libraries containing blunt-ends can be used directly in an adaptor ligation step. For some libraries, incorporation of a non-templated deoxyadenosine 5'-monophosphate (dAMP) onto the 3' end of blunted DNA fragments, a process known as dA-tailing, may be used to prevent concatamer formation during downstream ligation steps, and enable DNA fragments to be ligated to adaptors with complementary dT-overhangs. The desired adaptor ligated DNA size may be selected via gel electrophoresis before amplification by the polymerase chain reaction (PCR).

In some embodiments, the library preparation step may be accomplished outside of the flow cell. In other embodiments, the library preparation step may occur in the flow cell, using, e.g., transposon compositions immobilized to the solid support of the flow cell. In these embodiments, the transposon compositions may fragment and tag DNA fragments to prepare the library for seeding, clustering, amplification, and sequencing. More details regarding in-line sample preparation are provided in a later section of this disclosure.

Hybridizing a First Polynucleotide Library

In this embodiment, a negative or neutral charge is applied to a first electrode and a positive charge is applied to a second electrode. A first library is then delivered to a library sequencing region such as a lane flow cell. The library sequencing region contains the library capture surface with its associated plurality of electrodes. Because polynucleotides are negatively charged, the polynucleotides of the first library are attracted to the positively charged electrode and will predominantly hybridize with amplification primers proximate to the positive electrode. This localizes one library over one positively charged electrode or a set of positively charged electrodes.

Figure 2A:
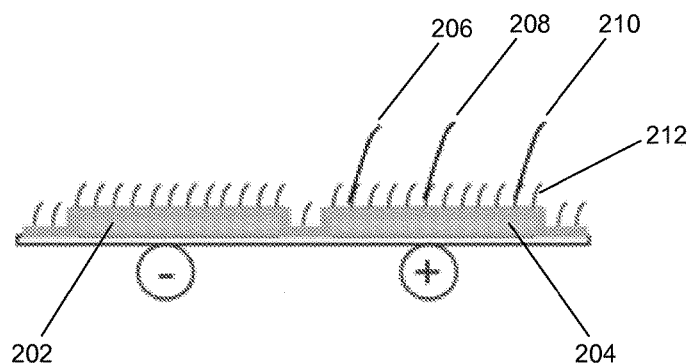
FIG. 2A shows a portion of a flow cell including two electrodes disposed on a solid support and an attachment layer, in accordance with some implementations.

FIG. 2A depicts a negative charge being applied to the first electrode 202 and a positive charge being applied to the second electrode 204. The polynucleotides 206, 208, 210 of the first library are then drawn to the library capture surface above the positive electrode 204 where they hybridize with the amplification primers 212 proximate to the positive electrode 204. Note that capture moieties other than primers may be used. Such moieties may be nucleic acid strands or other species.

Figure 2B:
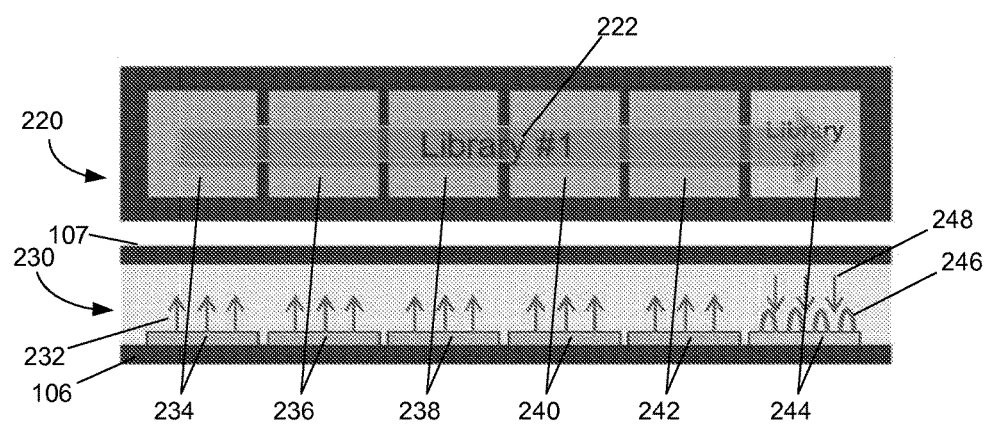
FIG. 2B shows a top and side view of a lane of a flow cell including six electrodes disposed on the flow cell, in accordance with some implementations.

FIG. 2B presents a top view 220 and a side view 230 of a library capture surface, such as a lane of a flow cell. FIG. 2B depicts the first polynucleotide library 222 being delivered down the lane of the flow cell. The side view 230 shows the repellant force 232 of the five electrodes 234, 236, 238, 240, 242 that are negatively charged, and the attractive force 248 of the last electrode 244 that is positively charged and the polynucleotides hybridizing to the last electrode 244. The polynucleotides 246 of the first library predominantly hybridize with the amplification primers proximate to the positively charged electrode 244.

In some implementations, the process applies a positive charge to two or more electrodes when a first library passes through the flow cell (or portion thereof) where the two or more activated electrodes reside. Other electrodes in the flow cell (or portion thereof) would not be activated.

Figure 2C:
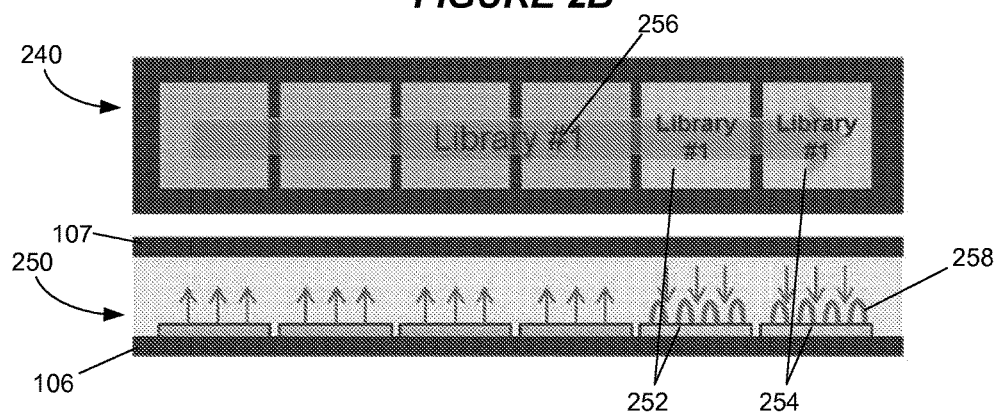
FIG. 2C shows a top and side view of a lane of a flow cell including six electrodes disposed on the flow cell, in accordance with some implementations.

FIG. 2C presents a top view 240 and a side view 250 of a library capture surface, such as a lane of a flow cell. FIG. 2C depicts the last two electrodes 252, 254 being activated with a positive charge as the first library 256 is delivered down the lane of the flow cell. In this embodiment, the polynucleotides of the first library 258 will hybridize predominantly with amplification primers located in the general area of the last two electrodes 252, 254. The two concurrently activated electrodes need not be adjacent to one another.

Hybridizing a Second Polynucleotide Library

Returning to the example of FIG. 2A, after polynucleotide members 206, 208, 210 of the first library are captured at a first location on the library capture surface, a negative charge is applied to the second electrode 204 and a positive charge is applied to the first electrode 202, and a second library is delivered through the flow cell. The polynucleotides of the second library will then predominantly hybridize with primers proximate to the first electrode.

Figure 3A:
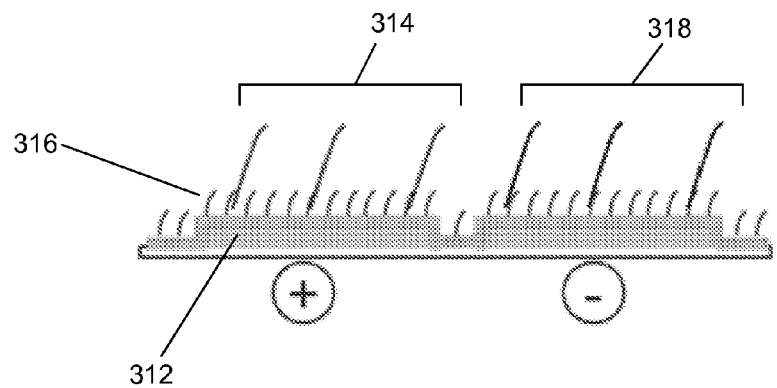
FIG. 3A shows a portion of a flow cell including two electrodes disposed on a solid support and an attachment layer, in accordance with some implementations.

FIG. 3A depicts the left electrode 312 being positively charged while the second library 314 is delivered over the electrodes, where the polynucleotides of the second library 314 then hybridize to amplification primers 316 near the left electrode 312. The result is that the polynucleotides of the first 318 and second 314 libraries are spatially isolated within a lane of a flow cell.

Figure 3B:
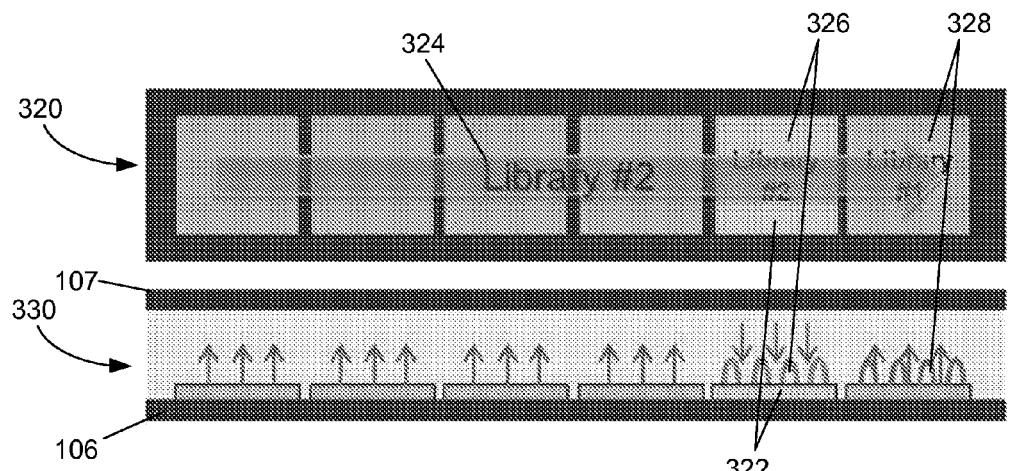
FIG. 3B shows a top and side view of a lane of a flow cell including six electrodes disposed on the flow cell, in accordance with some implementations.

FIG. 3B presents a top view 320 and a side view 330 of a library capture surface, such as a lane of a flow cell. FIG. 3B depicts an example of applying a positive charge to a second electrode 322 while delivering a second polynucleotide library 324 down the lane of the flow cell, accomplishing spatial isolation of two libraries 328, 326 within a lane of a flow cell.

Figure 3C:
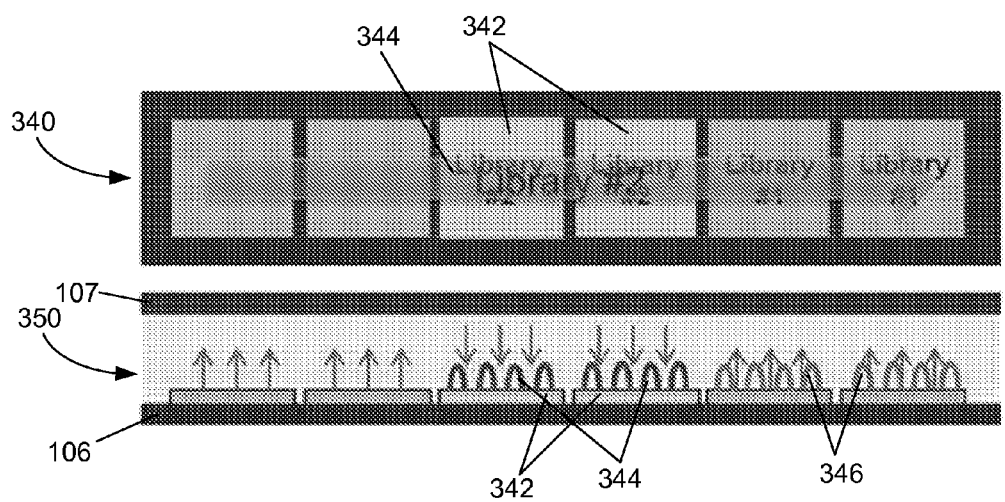
FIG. 3C shows a top and side view of a lane of a flow cell including six electrodes disposed on the flow cell, in accordance with some implementations.

FIG. 3C presents a top view 340 and a side view 350 of a library capture surface, such as a lane of a flow cell. FIG. 3C depicts an example of applying a positive charge to a second set of electrodes 342 while delivering a second polynucleotide library 344 down the lane of the flow cell, both accomplishing spatial isolation of two libraries 346, 344 within a lane of a flow cell.

In some embodiments, additional polynucleotide libraries may be delivered through the lane of the flow cell while activating different electrodes with positive charges. For example, a third electrode or a third set of electrodes may be positively charged while delivering a third library through the flow cell. Additional libraries can be delivered and selectively captured in the same manner.

Amplification and Sequencing

Once the two libraries have been hybridized in locations proximate to the electrodes, the remaining operations of a standard protocol for multiplexed sequencing may be performed. For example, cluster generation and sequencing may be executed in a manner that concurrently sequences all the captured libraries. Examples of these additional steps will be provided below.

Figure 3D:
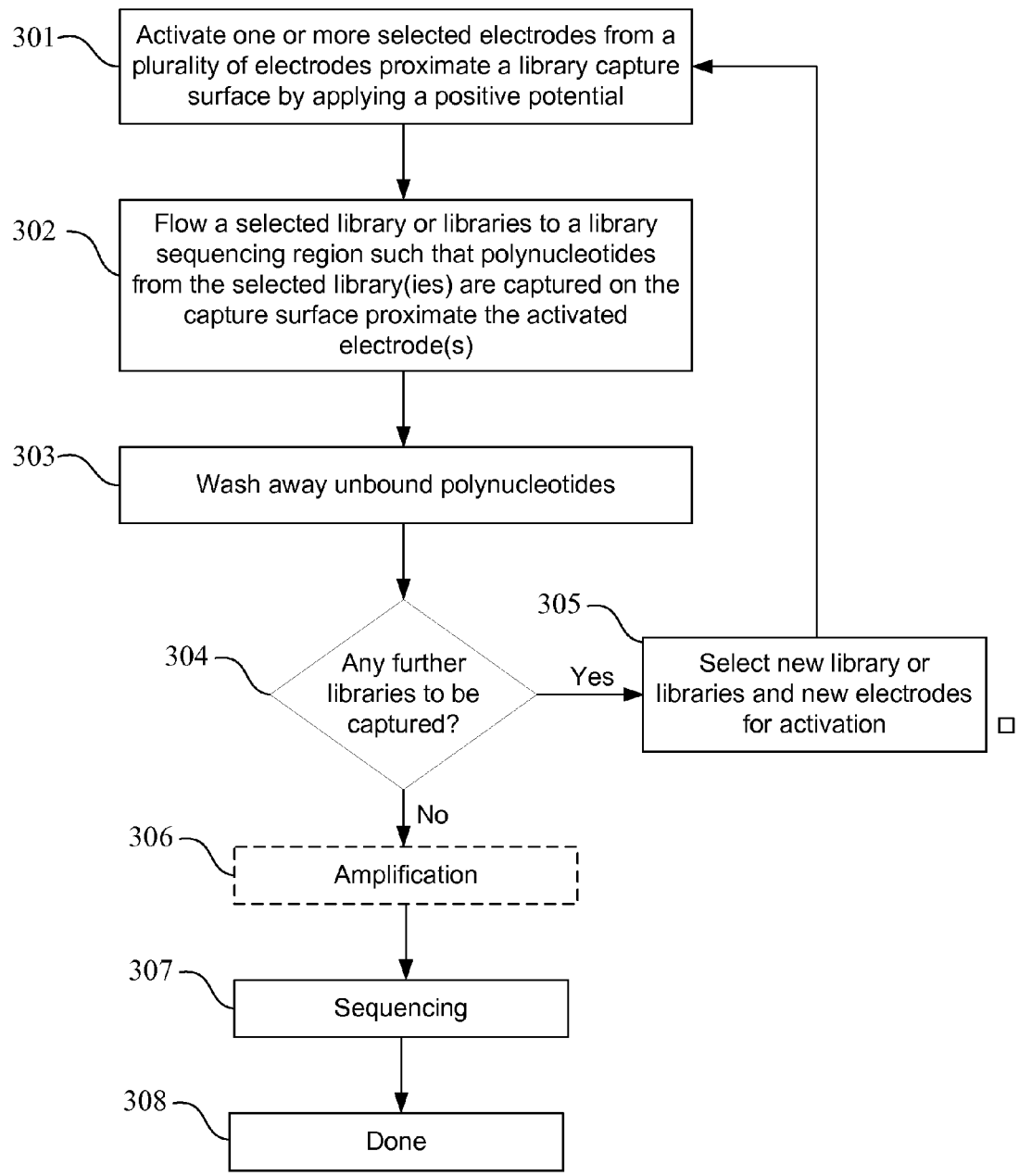
FIG. 3D shows a flow chart of a process of sequentially flowing one or more libraries through a library sequencing region while activating different electrodes for multiplexed sequencing of the one or more libraries, in accordance with some implementations.

FIG. 3D shows a flow chart of a process of sequentially flowing one or more libraries through a library sequencing region while activating different electrodes for multiplexed sequencing of the libraries. Initially, at block 301, one or more electrodes are selected and activated from a plurality of electrodes proximate a library capture surface by applying a positive potential. In some embodiments, a negative or neutral potential may be applied to the non-selected electrodes. At block 302, a selected library or libraries are flowed to a library sequencing region such that polynucleotides from the selected library or libraries are capture on the capture surface proximate the activated electrodes. Because the polynucleotides have a negative charge, they are attracted to the positively charged activated electrodes and will hybridize with the primers of the capture surface proximate the activated electrodes. At block 303, the unbound polynucleotides are washed away from the library sequencing region, leaving behind the polynucleotides that are hybridized to the capture surface primers proximate the library sequencing region. At block 304, a determination is made as to whether any further libraries are to be captured. If the answer is yes, then at block 305, a new library or libraries is selected to be flowed through the library sequencing region, and new electrodes are selected for activation. The process then returns to blocks 301, 302, and 303, where the new electrodes are activated by applying a positive potential, the new libraries are flowed through the library sequencing region such that polynucleotides of the new libraries are captured on the capture surface proximate the activated electrode, and the unbound polynucleotides are washed away. If the answer at block 304 is no, the process moves on to block 306, where the bound polynucleotides are amplified to form clusters proximate the electrodes. In some embodiments, the amplification step is optional. At block 307, the bound polynucleotides or clusters undergo sequencing to identify the nucleic acid sequences of the bound polynucleotides.

Applications

Some embodiments utilize separate electrodes to spatially isolate one library from another in a flow cell lane for multiplexed sequencing. Spatial isolation allows libraries to be distinguished from one another, so that more distinct libraries may be sequenced at one time on a given flow cell, ultimately reducing the sequencing time and cost for a DNA sample. Whereas current technology allows libraries to be distinguished by the lane of a flow cell where a library is located, the disclosed embodiments allow, e.g., 6-12 libraries to be clustered and sequenced in a single flow cell lane without barcoding.

Conventional mechanisms for distinguishing libraries often utilize barcoding, in which an index (or barcode) is attached to each polynucleotide of a library. The barcode is a unique nucleic acid sequence. Barcode identification requires that a sequencer read the barcode, which may result in some loss of signal. Additionally, the library preparation portion of the process must include steps that apply the same barcode to all members of a library. Some implementations disclosed herein reduce sequencing time by providing a method of spatially indexing multiple libraries without requiring that a barcode be attached to each polynucleotide of a library. This eliminates the time required to read the polynucleotide barcodes. This also reduces the number of reagents required to prepare a sample for sequencing, since the barcodes do not need to be attached to the polynucleotide members of the library.

Certain embodiments use both barcoding and spatial separation to separate libraries. In some embodiments, this permits high confidence that libraries are segregated, which is relevant because regulatory agencies typically require that diagnostic techniques contain rigorous safeguards against cross contamination. Further, use of barcoding and spatial separation together may allow larger numbers of libraries to be processed together by multiplexing.

Another advantage of the claimed systems and methods is that the amount of time required to capture the polynucleotide libraries in the flow cell may be reduced. Using current technology such as that embodied in an Illumina HiSeq® sequencer, typically more than 15 minutes is required for sufficient DNA from a library to be hybridized in the flow cell lane. Some embodiments of current technology have demonstrated that 15-50% of DNA is captured by the primers during hybridization over a 20 minute period. In these tests, capture efficiency may be estimated using obtained cluster density divided by input library concentration.

Figure 4:
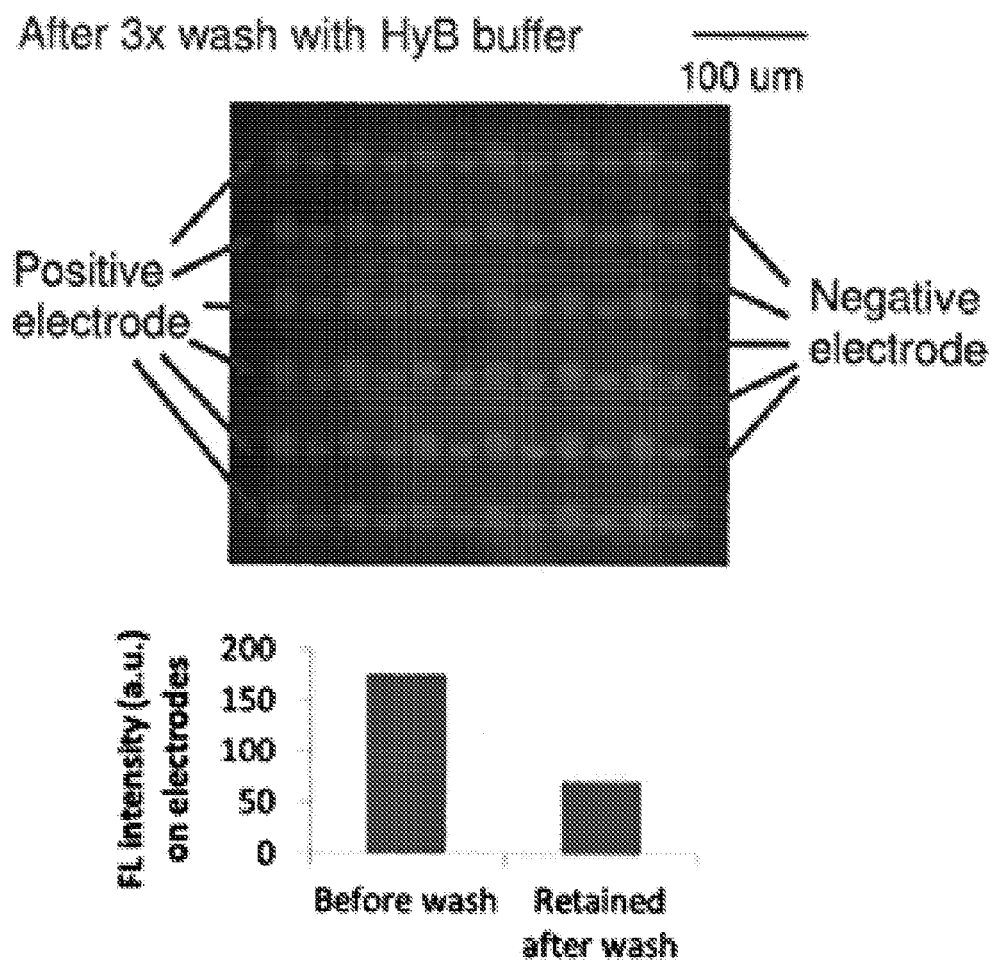
FIG. 4 shows the percentage of transported DNA that is captured when electrodes are used to capture the DNA, in accordance with some implementations.

Utilizing electrodes in some of the disclosed embodiments, sufficient hybridization of the libraries to the primers proximate to the electrodes may be accomplished in less than one minute. FIG. 4 demonstrates that in some embodiments, about 40% of the transported DNA may be captured by immobilized primers within one minute. This rapid hybridization time facilitates sequential introduction of multiple samples into a flow cell lane. Additionally, since a greater percentage of the polynucleotides that are delivered through the flow cell are captured and hybridized when the claimed systems and methods are used, a smaller sample is required.

Moreover, current capture efficiency without electrodes is sufficient due to high concentrations of amplification primers on the flow cell library capture surface. For example, current technology may employ paired end primers at a concentration of about 1000-5000 primers per square micrometer. Applying an electric field with electrodes can increase the speed of hybridization and/or enable the use of lower concentrations of target polynucleotides for flow cell capture-based sequencing methods where the concentration of capture primers for target polynucleotides is significantly lower, e.g., more than 100 times lower, than that of the concentration of paired end primers in a conventional flow cell.

Electrodes and Their Application in Sequencing
Electrical Properties

Generally, the electrodes should be designed and placed to apply a localized positive electrical field sufficiently great to pull polynucleotide molecules out of a fluid and onto a region of a library capture surface selectively activated positive electrical field. The material for the electrodes should allow reliable and efficient generation of such electric field. To accomplish this, the electrodes may have a conductance in the approximate range of about 250 nS-1 µS. In some embodiments, the electrodes are made of a high conductivity material such as a metal or a conductive oxide, e.g., gold or indium tin oxide (ITO). In some embodiments, the electrodes are made of silver, tin, titanium, copper, platinum, palladium, polysilicon, or carbon. The electrodes may take any shape suitable for capturing and spatially isolating captured nucleic acids. For example, the electrodes may be substantially round-shaped or polygonally shaped, e.g., rectangular. In some embodiments, the electrodes are shaped as rectangles that span the width of a flow cell or a lane of a flow cell on which the electrode is disposed. In such embodiments, two to twelve rectangular-shaped electrodes are disposed in a line along the solid support of the flow cell, along the direction of fluid flow, e.g., perpendicular to the lanes of the flow cell.

Application of an electric potential to an electrode may be characterized by various parameters. For example, the positive voltage applied to an activated electrode may be in the approximate range of about 0.5-3V, depending on the electrode material and the polynucleotide acid carrier fluid used. In particular, the applied voltage may be below the voltage at which electrolysis of water occurs, and at or above the voltage at which the redox reaction of a reducing agent additive occurs. The current produced during the application of the positive electric potential to the electrode may be in the approximate range of about 250 nA-5 uA. The current density produced may be in the approximate range of about 5-20 uA/mm$^2$. The electric field adjacent the electrode and amplification primers may be in the approximate range of about 10-200V/cm.

In certain embodiments, rectangular electrodes have a width (direction perpendicular to the direction of flow) that spans most or all of the width of a lane of a flow cell. Further, the electrodes may have a length (direction of flow) that allows at least about five electrodes disposed along the length of a flow cell lane. As an example, an electrode may have a width of between about 1 um and 20 mm, and have a length of between about 1 um and 100 mm. The total surface area of an electrode may be between about 100 um$^2$ and 200 mm$^2$. The separation between adjacent electrodes should be sufficient to prevent charge applied to one electrode from leaking to an adjacent electrode. In certain embodiments, the minimum separation distance is between about 10 micrometers and 1 millimeter, or between about 20 and 50 micrometers.

Figure 5:
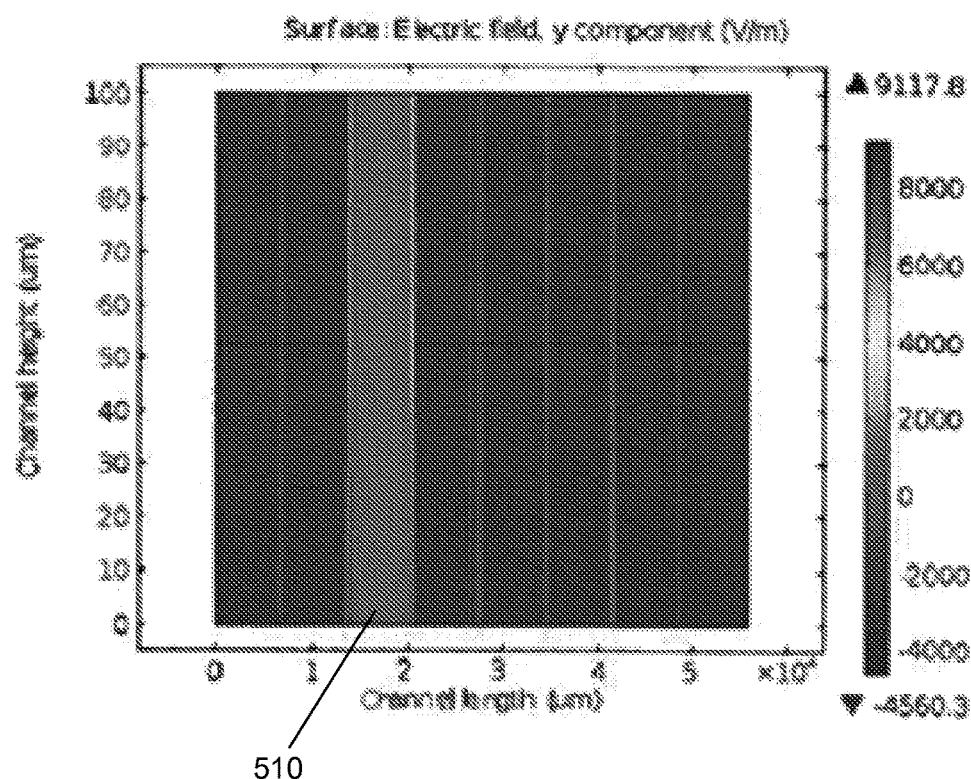
FIG. 5 shows the electric field distribution along the length and height of the flow cell when an electrode is positively charged, in accordance with some implementations.

FIG. 5 illustrates that in some flow cell designs, the electric field generated by an electrode 510 is approximately constant across the height of the flow cell lane from the bottom to the top of the flow cell. Further, examples of electrode configurations and dimensions are described in the Examples section of the disclosure below.

Multiplexed Sequencing of Multiple Libraries

Spatial isolation of libraries onto different electrodes by an electric field provides a new dimension to multiplexing. Using multiple flow cell lanes introduces one dimension of multiplexing, as different libraries may be loaded into different lanes to spatially separate the different libraries. A flow cell with eight lanes may be used to sequence eight different libraries at one time.

Utilizing barcoding, in which an index (or barcode) is attached to each polynucleotide of a library, introduces another dimension of multiplexing. Therefore, if, within a single flow cell lane, eight different libraries are introduced, each library having a different barcode attached to its polynucleotides, then the flow cell with eight lanes and barcoding may be used to sequence 64 different libraries at one time.

Introducing the spatial separation onto different electrodes of a flow cell lane by an electric field provides yet another dimension to multiplexing. A flow cell 600 such as the one depicted in FIG. 6, which has eight flow cell lanes 610 and eight electrodes 620, and which utilizes eight different barcodes, allows for sequentially loading eight sets of libraries into each flow cell lane, where each set of libraries includes eight libraries that are distinguishable by their barcodes. Such a flow cell is able to sequence 512 different libraries at one time.

In Line Sample Preparation

In some embodiments, the library preparation, wherein a DNA sample is fragmented to a designated length and adapters are ligated to the ends of the fragments, is performed outside of the flow cell. Certain methods currently used for fragmentation and tagging of double-stranded DNA for use in next-generation sequencing may be wasteful of the DNA, require expensive instruments for fragmentation, and the procedures for fragmentation, tagging and recovering tagged DNA fragments are difficult, tedious, laborious, time-consuming, inefficient, costly, require relatively large amounts of sample nucleic acids. In addition, many of these methods generate tagged DNA fragments that are not fully representative of the sequences contained in the sample nucleic acids from which they were generated.

In some embodiments described herein, some procedures required for library preparation are accomplished in the lane of the flow cell, as described in U.S. patent application Ser. No. 13/790,220, which is incorporated by reference in its entirety herein. In these embodiments, transposon compositions immobilized to a solid support are used to fragment and tag the DNA.

In these embodiments, the method of preparing an immobilized library of tagged DNA fragments comprises: (a) providing a solid support having transposome complexes immobilized thereon, wherein the transposome complexes comprise a transposase bound to a first polynucleotide, the first polynucleotide comprising (i) a 3' portion comprising a transposon end sequence, and (ii) a first tag comprising a first tag domain; and (b) applying a target DNA to the solid support under conditions whereby the target DNA is fragmented by the transposome complexes, and the 3' transposon end sequence of the first polynucleotide is transferred to a 5' end of at least one strand of the fragments; thereby producing an immobilized library of double-stranded fragments wherein at least one strand is 5'-tagged with the first tag. In some embodiments, the transposome complexes comprise a second polynucleotide comprising a region complementary to said transposon end sequence. The methods can further comprise (c) providing transposome complexes in solution and contacting the transposome complexes with the immobilized fragments under conditions whereby the target DNA is fragmented by the transposome complexes in solution; thereby obtaining immobilized nucleic acid fragments having one end in solution. In some embodiments, the transposome complexes in solution can comprise a second tag, such that the method generates immobilized nucleic acid fragments having a second tag, the second tag in solution. The first and second tags can be different or the same.

In some embodiments, the solid support may include a library of tagged DNA fragments immobilized thereon. For example, the solid supports may have transposome complexes immobilized thereon, wherein the transposome complexes comprise a transposase bound to a first polynucleotide, the polynucleotide comprising (i) a 3' portion comprising a transposon end sequence, and (ii) a first tag comprising a first tag domain.

In some embodiments, a flow cell may be generated by immobilizing a plurality of transposome complexes to a solid support, the transposome complexes comprising a transposase bound to a first polynucleotide, the first polynucleotide comprising (i) a 3' portion comprising a transposon end sequence, and (ii) a first tag comprising a first tag domain.

Figure 7:
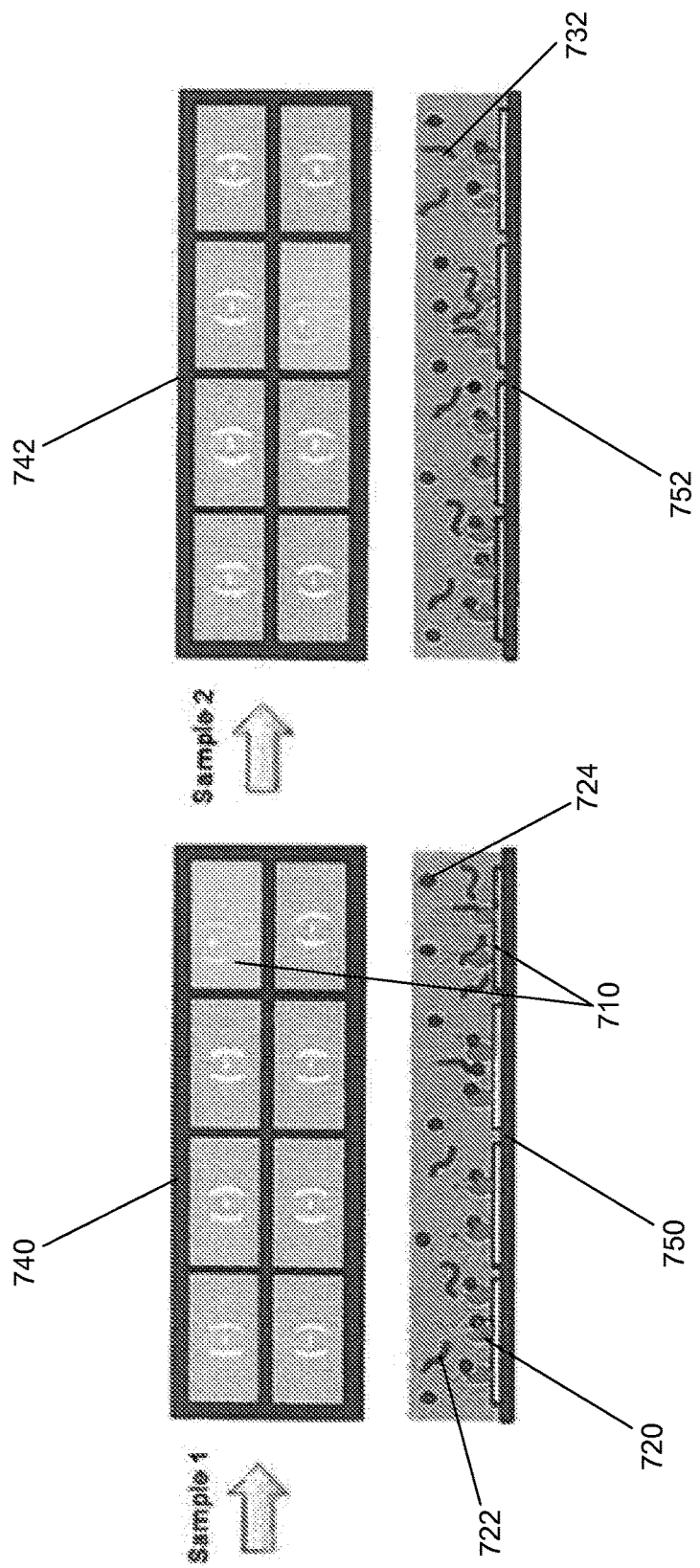
FIG. 7 shows a flow cell used for in-line sample preparation using immobilized Tn5 transposons, in accordance with some implementations.

As depicted in FIG. 7, an electric field generated by one or more electrodes 710 in a flow cell may facilitate inline sample preparation using immobilized Tn5 transposons 720. For example, a first genomic DNA sample 722 may be introduced into the flow cell while one electrode in a target area is at a positive or zero potential and while the rest of the electrodes outside the target area are at a negative potential. The immobilized Tn5 transposons will only incorporate adaptors onto genomic DNA in the target area. In FIG. 7, the upper panels 740, 742 present top views of two lanes of a flow cell and the lower panels 750, 752 present side views of the same flow cell cut through the lanes in having a positively charged electrode. Transposons 720 are shown as immobilized egg-shaped proteins and sample DNA 722 is shown as string-like structures. Positively-charged transposon inhibitors 724, which are shown as black dots in FIG. 7, are attracted to negative electrodes to inhibit adaptor incorporation outside of the target region 710. The left panels of FIG. 7 illustrate the flow cell lanes when a first set of polynucleotides 722 is introduced and the right panels illustrate the flow cell lanes when a second set of polynucleotides 732 is introduced. The next set may be introduced with activation of a third electrode or set of electrodes, and so forth. The polynucleotides in a set may belong to a library, a sample, etc. In other embodiments, a positively charged Tn5 inhibitor 724 can be simultaneously delivered and attracted to negatively charged electrodes to inhibit adaptor incorporation outside of the target area.

Fluid Medium Provided to Library Sequencing Region

The polynucleotides of a library are delivered to the library sequencing region of a flow cell or other sequencing device via a carrier fluid. The polynucleotides are carried along with fluid and may randomly attach to the capture surface along the way. However, most of the polynucleotides are captured at a region (or regions) of the capture surface where one or more electrodes are activated with a positive charge. The positive electric field exerts an attractive electrostatic force on the polynucleotides and pulls them out of the carrier fluid and onto the capture surface.

The carrier fluid may contain water and various additives to buffer and otherwise stabilize the polynucleotides of the library. In some embodiments, the buffer used for electric field directed hybridization may be a relatively low conductivity buffer with a reducing agent, and having a pH in the range of about 6-9. One approach to designing a carrier fluid for electric field hybridization uses a buffer suitable for DNA electrophoresis (such as one containing Tris, Bis-Tris, or imidazole—e.g., 1×TBE) to which is added a reducing agent. The electrophoresis buffer provides suitable conductivity and pH such that DNA is negatively charged. The reaction of reducing agent, when exposed to an electric field from the electrodes, provides current that can drive DNA movement without inducing electrolysis of water. In one embodiment, the carrier fluid contains 1×TBE (89 Mm Tris, 89 mM Boric acid, 2 mM EDTA, pH=8.3).

Figure 8:
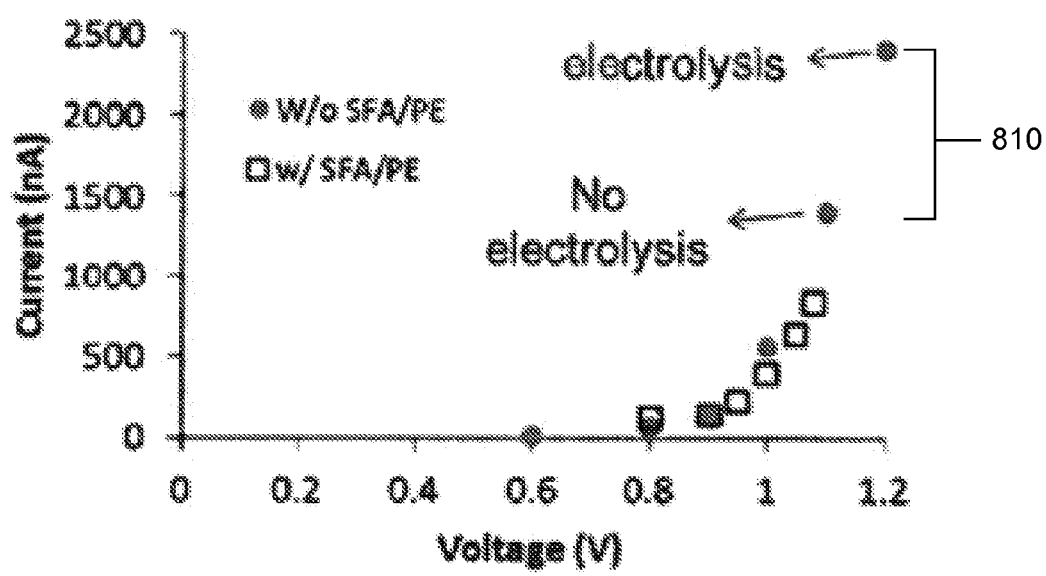
FIG. 8 shows the current to voltage relationship in the flow cell and the point at which electrolysis occurs, in accordance with some implementations.

In some embodiments, protective chemistry is utilized in the buffer solution to prevent damage to the primers of the capture surface and to the polynucleotides in the library. In the absence of a protective reducing agent in the buffer solution, application of an electrical current to the buffer may, at a sufficient voltage, cause some electrolysis of water molecules, producing molecular oxygen, which may damage the nucleic acid amplification primers and/or the polynucleotide library. Damage to the amplification primers may cause them to lose the capability to bind to the complementary sequences of the library polynucleotides. FIG. 8 demonstrates how incrementing the voltage increases the electrical current produced and the point at which electrolysis begins to occur. In theory, the library processing system could include a voltage controller to prevent the sequencing region voltage from exceeding a threshold after which electrolysis occurs. As illustrated in FIG. 8, however, the transition 810 between electrolysis and no electrolysis can be very abrupt.

Adding to the buffer a protective reducing agent, which undergoes electrolysis at a potential lower than the potential at which water undergoes electrolysis, permits the electric field to be generated for capture/hybridization of the polynucleotides without generating molecular oxygen. Including an appropriate reducing agent, such as beta-mercaptoethanol, produces a protective redox reaction that keeps the local potential in the sequencing region below the potential at which oxygen forms. The process generates sufficient potential to induce mobility of polynucleotides toward the capture surface but with substantially reduced generation of molecular oxygen. Other reducing agents that may be used include: dithiothreitol, alpha-thiolglycerol, hydroquinone, or any electroactive species with an oxidation potential lower than that of water on the electrodes used in the disclosed embodiments.

In many implementations, the buffer employs a relatively high concentration of reducing agent to produce sufficient current; however, the upper concentration limit may be limited based on (a) solubility of the reducing agent and (b) addition of the reducing agent cannot inducing significant change (<1 pH unit) to the buffer pH. For 2-mercaptoethanol, an example of a suitable range is about 0.7-2.8M; for hydroquinone an example of a suitable range is about be 100-500 mM.

In one example, a reducing agent used in combination with 1×TBE buffer on Gold electrodes is 1.4M 2-mercaptoethanol and 10 mM Dithiothreitol (although just 1.4M 2-mercaptoethanol may be sufficient). In another example, a reducing agent used in combination with 1×TBE buffer on ITO electrode is 250 mM hydroquinone.

In some embodiments, two or more reducing agents may be used together in the buffer. Generally, in some embodiments, the potential applied to attract the polynucleotides toward the capture surface is above the potential at which the reducing agent undergoes a redox reaction, but below the potential at which electrolysis of water occurs on the specific electrode material. The redox reaction of the protective agent moderates the actual potential experienced within the sequencing region, preventing that potential from reaching a level at which water electrolysis may occur. Further, the products of the protective redox reaction should be benign to the library polynucleotides and any oligonucleotides on the capture surface. An example of a benign byproduct is a disulfide produced by oxidation of a mercaptan.

Figure 9:
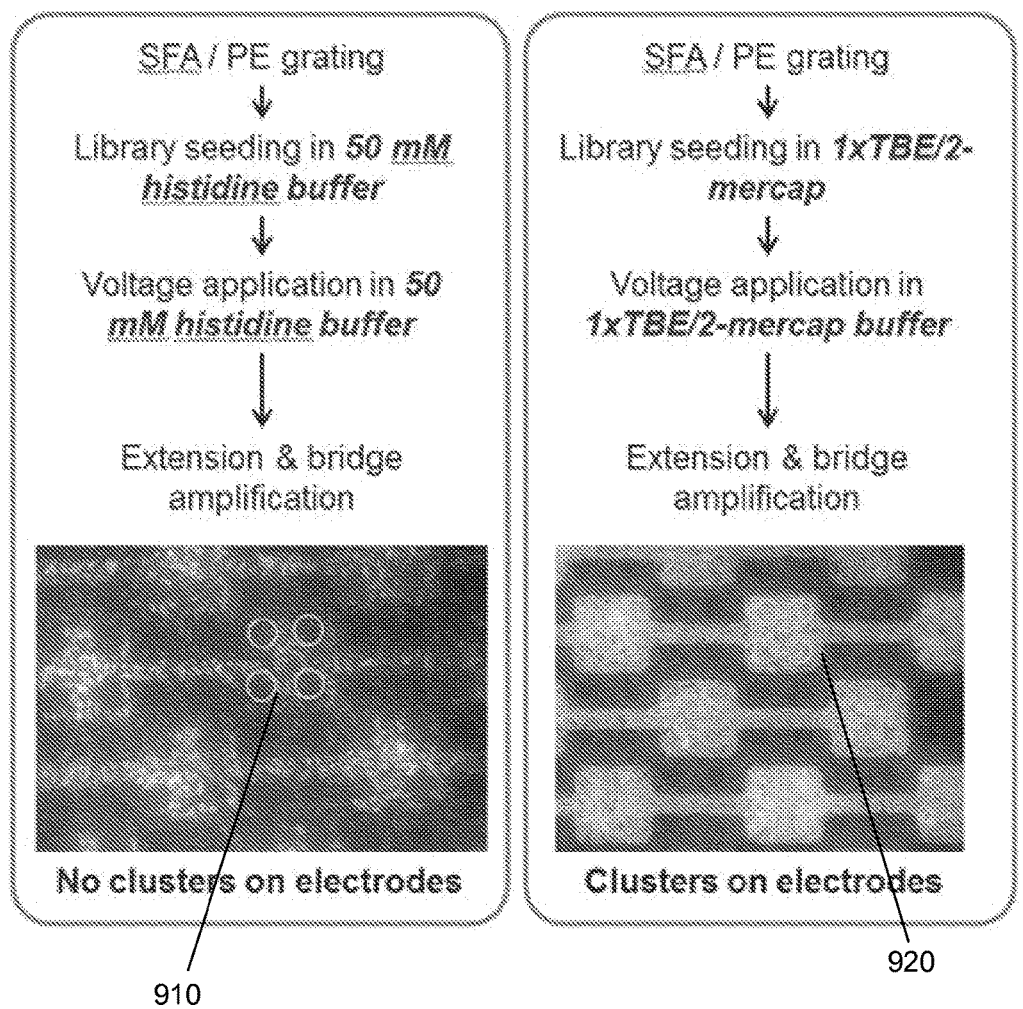
FIG. 9 shows the effect of including a reducing agent (2-mercap) in the buffer on the extent to which DNA clusters form over the electrodes, in accordance with some implementations.

FIG. 9 demonstrates the protective effect of adding a reducing agent, such as 2-mercaptoethanol (beta-mercaptoethanol), to the buffer. The circles 910, 920 indicate where electrodes are exposed to solution and where there is electric field. Voltage application in a histidine buffer solution without reducing agent leads to electrolysis, which damages the amplification primers and negatively impacts their ability to bind to the library polynucleotides and support bridge amplification. Voltage application in a 1×TBE/2-mercaptoethanol buffer generates current through the oxidation of 2-mercaptoethanol, which is less damaging to primers; hence, the primers can support downstream cluster generation.

Cross-contamination

Hybridization using an electric field may result in some cross-contamination if there is insufficient repulsion from the negative electrodes such that a polynucleotide hybridizes with a capture primer near a negative electrode. Another potential source of cross-contamination is when a hybridized polynucleotide, which hybridized with a primer when the nearby electrode had a positive charge, is removed from the electrode when a negative charge is subsequently applied to the nearby electrode.

Figure 10A:
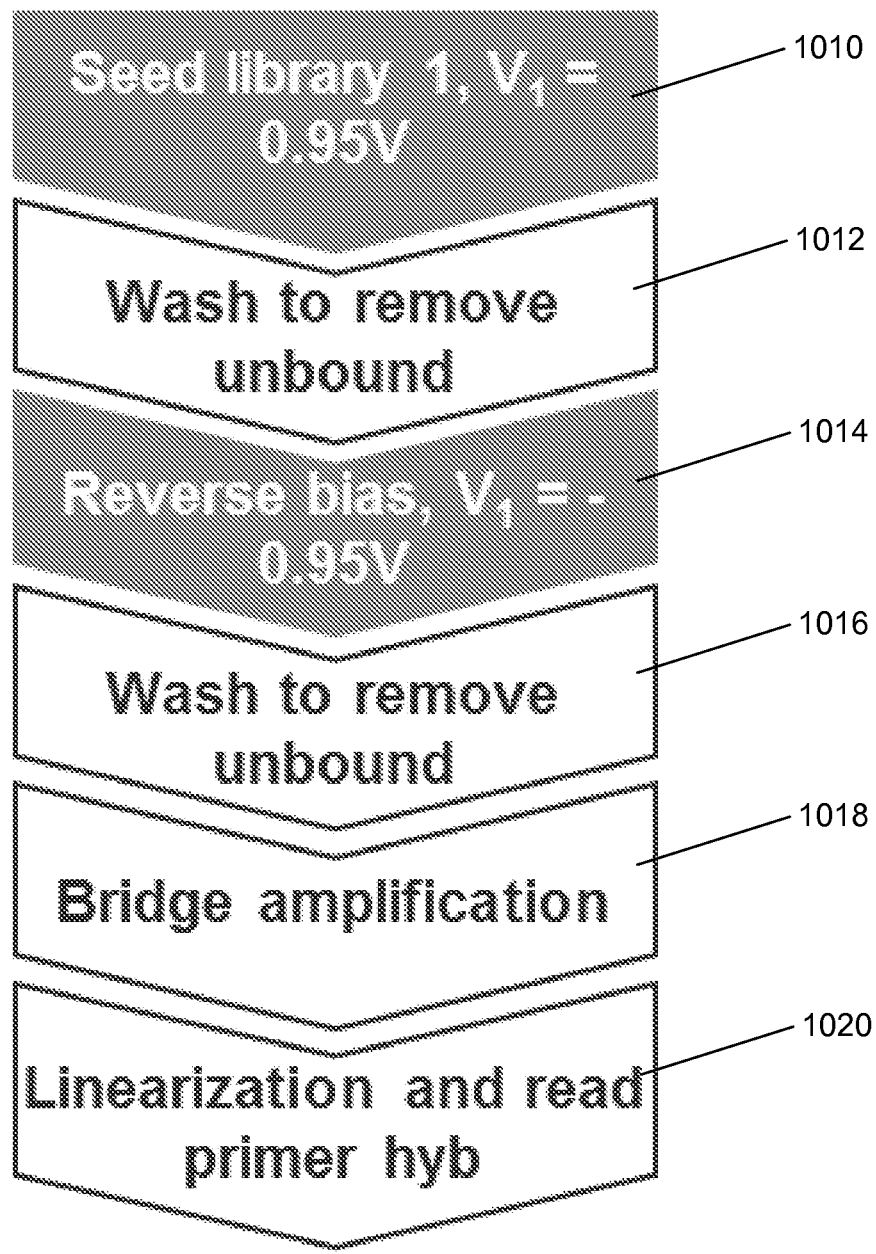
FIG. 10A shows a flow chart of a process of seeding a DNA library while a set of electrodes is positively charged, followed by reversing the bias of the set of electrodes, to demonstrate the extent of cross-contamination of clusters on the other set of electrodes, in accordance with some implementations.

FIG. 10A presents a flow chart in which these sources of contamination are addressed by controlling flow to a flow cell or other sequencing region and by controlling potential to multiple electrodes in the flow cell. Initially, in block 1010, a solution containing a seed library flows over an electrode while the electrode has a potential of, e.g., +0.95V. Thereafter, at block 1012, the sequencing region, including the electrodes, is washed to remove unbound polynucleotides from the seed library. Next, at block 1014, the controller applies a negative bias (e.g., −0.95 V) to the electrode, while applying a positive bias to another electrode and flowing a different library over the electrodes. Thereafter, at block 1016, the sequencing region is again washed to remove unbound polynucleotides. The process of applying a positive voltage to another electrode and a negative voltage to the remaining electrodes followed by washing may be repeated for one or more additional libraries. After all libraries are captured, the system sequences them simultaneously. In the embodiment of FIG. 10A, this is accomplished by bridge amplification at block 1018, followed by linearization and sequencing at block 1020.

Figure 10B:
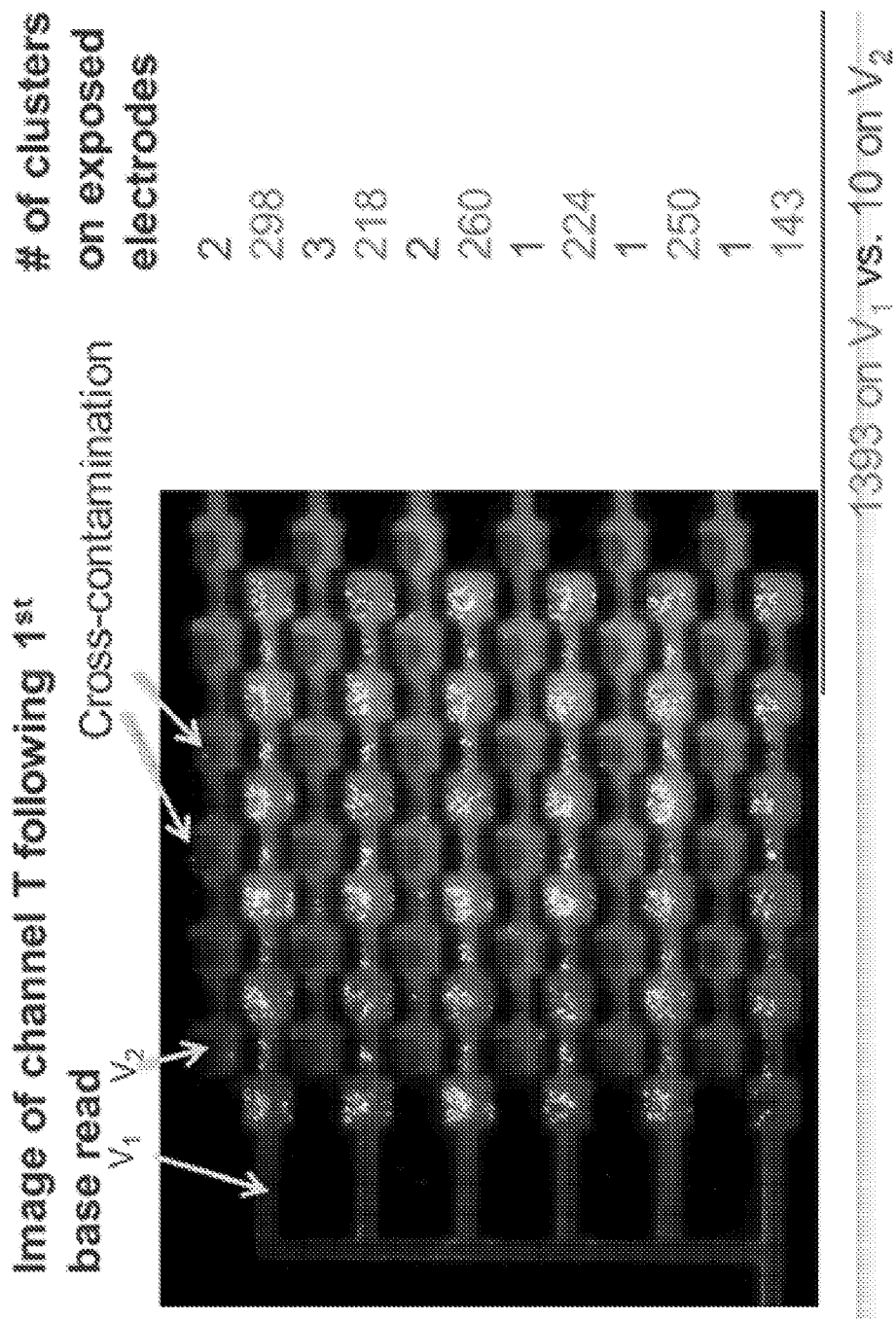
FIG. 10B demonstrates the amount of cross-contamination resulting from the process described in FIG. 10A, in accordance with some implementations.

FIG. 10B shows an image of channel T following the first base read (T) after the flow described in FIG. 10A is executed. The figure shows that applying a 0.95V charge to the target electrodes while delivering the polynucleotide library through a flow cell, followed by reversing the charge resulted in only 0.7% rate of cross-contamination onto the non-target electrodes in this example. Further improvement can be achieved by refining the capture and washing operations.

Capture Conditions for Different Electrode Materials

Figure 11A:
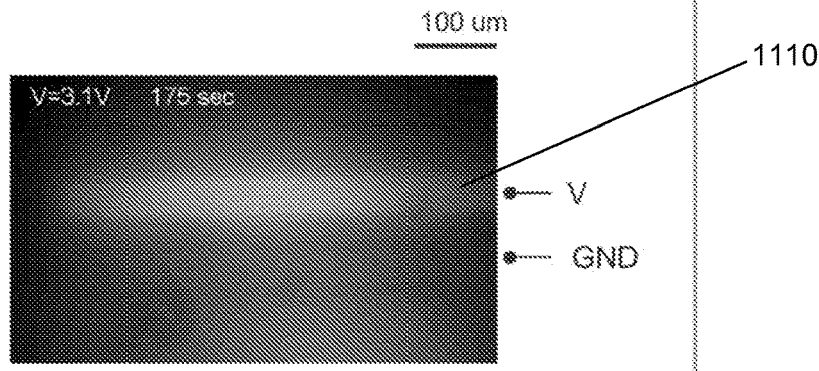
FIG. 11A shows the voltage at which polynucleotides will concentrate over the electrodes when Indium tin oxide (ITO) electrodes are used, in accordance with some implementations.
Figure 11B:
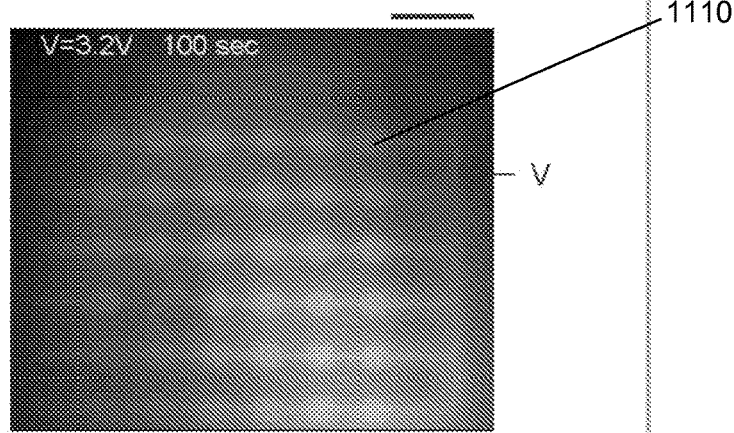
FIG. 11B shows the voltage at which polynucleotides will concentrate over the electrodes when ITO electrodes are used, in accordance with some implementations.
Figure 12A:
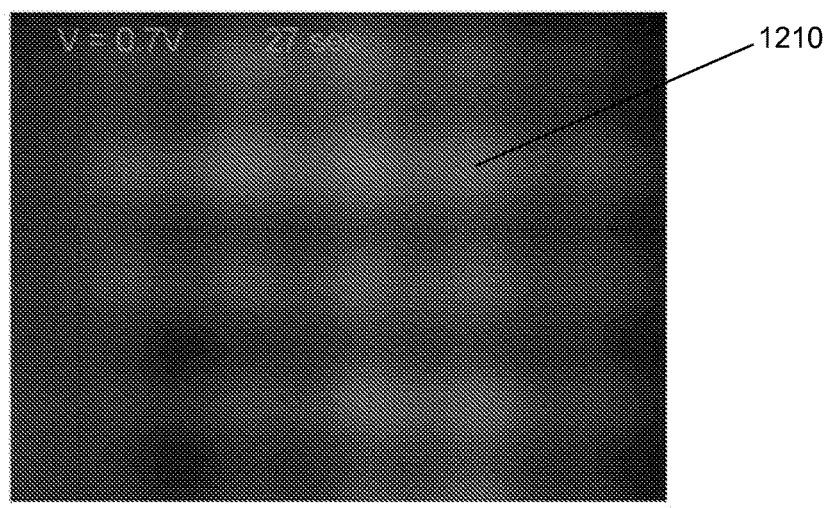
FIG. 12A shows the voltage at which polynucleotides will concentrate over the electrodes when ITO electrodes are used and when 250 mM hydroquinone is added to the buffer, in accordance with some implementations.
Figure 12B:
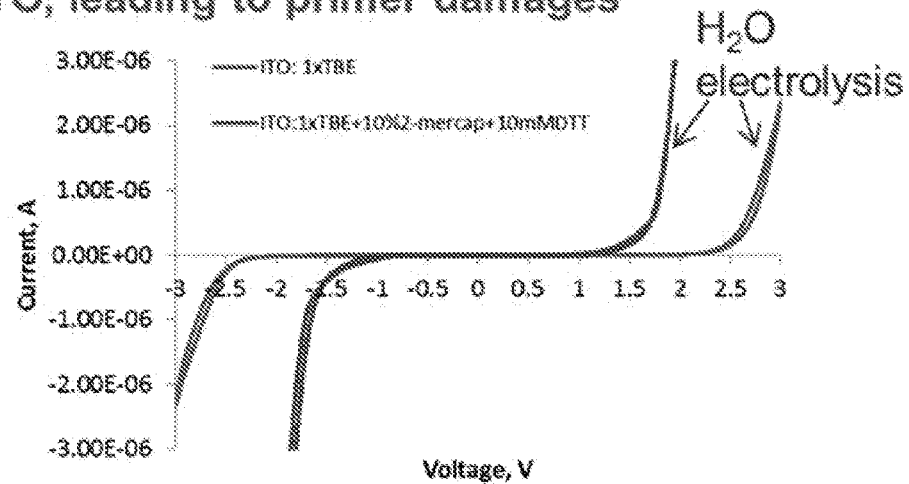
FIG. 12B shows the current to voltage relationship when ITO electrodes are used in a buffer containing 10% 2-mercaptoethanol and in a buffer not containing any 2-mercaptoethanol, in accordance with some implementations.
Figure 12C:
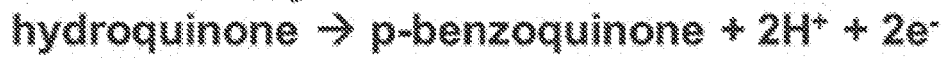
FIG. 12C shows the current to voltage relationship when ITO electrodes are used in a buffer containing hydroquinone, in accordance with some implementations.
Figure 12C:
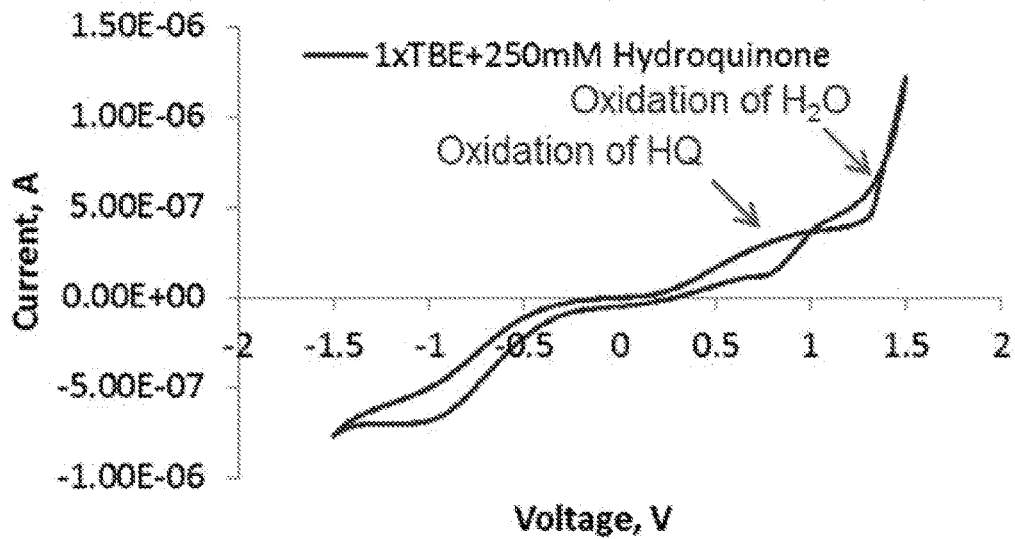

As explained, gold electrodes may be used to produce the electric field to manipulate the polynucleotide libraries being delivered through the flow cell. In other embodiments, ITO electrodes on glass slides may be used. Whereas a voltage of approximately 0.9-1V is sufficient to attract the polynucleotides to the capture primers near the charged electrode when the electrode is made of gold, FIGS. 11A and 11B illustrate that a voltage of approximately 3V may concentrate DNA on ITO electrodes 1110 in a buffer without reducing agent. FIG. 12A demonstrates that the addition of hydroquinone to the buffer enables DNA concentration at a voltage of less than 1V using ITO electrodes 1210. FIGS. 12B and 12C demonstrate that oxidation of hydroquinone occurs at a voltage lower than 1V (well below the potential at which water electrolyzes), which means that hydroquinone is a suitable reducing agent for the buffer when ITO electrodes are used.

Bridge Amplification

Once the library polynucleotides have been selectively captured as described above, they may be sequenced by an appropriate technique. In some embodiments, the captured polynucleotides are amplified to form clusters which are then sequenced by synthesis. This is not the only sequencing technique suitable for use with this disclosure, but it will be explained as an example in this and the following section.

The captured target polynucleotides hybridize with the amplification primers on the library capture surface, captured the captured polynucleotides can be amplified. Optionally, the amplification comprises using the primers on the support. Alternatively, the amplification can comprise using one primer in solution and one primer on the support. In some embodiments, amplification produces clusters of amplified target nucleic acid molecules. Generally amplification reactions use at least two amplification oligonucleotides, often denoted 'forward' and 'reverse' primers. Generally amplification oligonucleotides are single stranded polynucleotide structures. They may also contain a mixture of natural or non-natural bases and also natural and non-natural backbone linkages, provided, at least in some embodiments, that any non-natural modifications do not permanently or irreversibly preclude function as a primer-that being defined as the ability to anneal to a template polynucleotide strand during conditions of an extension or amplification reaction and to act as an initiation point for the synthesis of a new polynucleotide strand complementary to the annealed template strand. Primers may additionally comprise non-nucleotide chemical modifications, for example to facilitate covalent attachment of the primer to a support. Certain chemical modifications may themselves improve the function of the molecule as a primer or may provide some other useful functionality, such as providing a cleavage site that enables the primer (or an extended polynucleotide strand derived therefrom) to be cleaved from a support.

Nucleic acid amplification includes the process of amplifying or increasing the numbers of a nucleic acid template and/or of a complement thereof that are present, by producing one or more copies of the template and/or or its complement. Amplification can be carried out by a variety of known methods under conditions including, but not limited to, thermocycling amplification or isothermal amplification. For example, methods for carrying out amplification are described in U.S. Publication No. 2009/0226975; WO 98/44151; WO 00/18957; WO 02/46456; WO 06/064199; and WO 07/010251; which are incorporated by reference herein in their entireties. Thus, amplification can occur on the surface to which the nucleic acid molecules are attached. This type of amplification can be referred to as solid phase amplification, which when used in reference to nucleic acids, refers to any nucleic acid amplification reaction carried out on or in association with a surface (e.g., a support). For example, all or a portion of the amplified products are synthesized by extension of an immobilized primer. Solid phase amplification reactions are analogous to standard solution phase amplifications except that at least one of the amplification oligonucleotides is immobilized on a surface (e.g., a solid support).

Solid-phase amplification may comprise a nucleic acid amplification reaction comprising only one species of oligonucleotide primer immobilized to a surface. Alternatively, the surface may comprise a plurality of first and second different immobilized oligonucleotide primer species. Solid-phase amplification may comprise a nucleic acid amplification reaction comprising one species of oligonucleotide primer immobilized on a solid surface and a second different oligonucleotide primer species in solution. Solid phase nucleic acid amplification reactions generally comprise at least one of two different types of nucleic acid amplification, interfacial and surface (or bridge) amplification. For instance, in interfacial amplification, the solid support comprises a template nucleic acid molecule that is indirectly immobilized to the solid support by hybridization to an immobilized oligonucleotide primer, the immobilized primer may be extended in the course of a polymerase-catalyzed, template-directed elongation reaction (e.g., primer extension) to generate an immobilized polynucleotide molecule that remains attached to the solid support. After the extension phase, the nucleic acids (e.g., template and its complementary product) are denatured such that the template nucleic acid molecule is released into solution and made available for hybridization to another immobilized oligonucleotide primer. The template nucleic acid molecule may be made available in 1, 2, 3, 4, 5 or more rounds of primer extension or may be washed out of the reaction after 1, 2, 3, 4, 5 or more rounds of primer extension.

In surface (or bridge) amplification, an immobilized nucleic acid molecule hybridizes to an immobilized oligonucleotide primer. The 3' end of the immobilized nucleic acid molecule provides the template for a polymerase-catalyzed, template-directed elongation reaction (e.g., primer extension) extending from the immobilized oligonucleotide primer. The resulting double-stranded product "bridges" the two primers and both strands are covalently attached to the support. In the next cycle, following denaturation that yields a pair of single strands (the immobilized template and the extended-primer product) immobilized to the solid support, both immobilized strands can serve as templates for new primer extension.

Optionally, amplification of the adapter-target-adapters or library of nucleic acid sequences results in clustered arrays of nucleic acid colonies, analogous to those described in U.S. Pat. No. 7,115,400; U.S. Publication No. 2005/0100900; WO 00/18957; and WO 98/44151, which are incorporated by reference herein in their entireties. Clusters and colonies are used interchangeably and refer to a plurality of copies of a nucleic acid sequence and/or complements thereof attached to a surface. Typically, the cluster comprises a plurality of copies of a nucleic acid sequence and/or complements thereof, attached via their 5' termini to the surface. The copies of nucleic acid sequences making up the clusters may be in a single or double stranded form.

Clusters may be detected, for example, using a suitable imaging means, such as, a confocal imaging device or a charge coupled device (CCD) camera. Exemplary imaging devices include, but are not limited to, those described in U.S. Pat. Nos. 7,329,860; 5,754,291; and 5,981,956; and WO 2007/123744, each of which is herein incorporated by reference in its entirety. The imaging means may be used to determine a reference position in a cluster or in a plurality of clusters on the surface, such as the location, boundary, diameter, area, shape, overlap and/or center of one or a plurality of clusters (and/or of a detectable signal originating therefrom). Such a reference position may be recorded, documented, annotated, converted into an interpretable signal, or the like, to yield meaningful information. The signal may, for instance, take the form of a detectable optical signal emanating from a defined and identifiable location, such as a fluorescent signal, or may be a detectable signal originating from any other detectable label as provided herein. The reference position of a signal generated from two or more clusters may be used to determine the actual physical position on the surface of two clusters that are related by way of being the sites for simultaneous sequence reads from different portions of a common target nucleic acid.

Sequencing by Synthesis

Following amplification, the amplified target extension products or target nucleic acids can be sequenced. Optionally, the sequencing includes sequencing-by-synthesis or sequencing-by-ligation.

Sequencing by synthesis, for example, is a technique wherein nucleotides are added successively to a free 3' hydroxyl group, typically provided by annealing of an oligonucleotide primer (e.g., a sequencing primer), resulting in synthesis of a nucleic acid chain in the 5' to 3' direction. These and other sequencing reactions may be conducted on the herein described surfaces bearing nucleic acid clusters. The reactions comprise one or a plurality of sequencing steps, each step comprising determining the nucleotide incorporated into a nucleic acid chain and identifying the position of the incorporated nucleotide on the surface. The nucleotides incorporated into the nucleic acid chain may be described as sequencing nucleotides and may comprise one or more detectable labels. Suitable detectable labels, include, but are not limited to, haptens, radionucleotides, enzymes, fluorescent labels, chemiluminescent labels, and/or chromogenic agents. One method for detecting fluorescently labeled nucleotides comprises using laser light of a wavelength specific for the labeled nucleotides, or the use of other suitable sources of illumination. The fluorescence from the label on the nucleotide may be detected by a CCD camera or other suitable detection means. Suitable instrumentation for recording images of clustered arrays is described in WO 07/123744, the contents of which are incorporated herein by reference herein in its entirety.

Various additional aspects regarding sequencing by synthesis procedures and methods that can be utilized with the systems and devices herein are described in, e.g., W004018497, W004018493 and U.S. Pat. No. 7,057,026 (nucleotides), W005024010 and W006120433 (polymerases), W005065814 (surface attachment techniques), and WO 9844151, W006064199 and W007010251, the contents of each of which are incorporated herein by reference in their entirety.

Optionally, cycle sequencing is accomplished by stepwise addition of reversible terminator nucleotides containing, for example, a cleavable or photobleachable dye label as described, for example, in U.S. Pat. Nos. 7,427,673; 7,414,116; WO 04/018497; WO 91/06678; WO 071123744; and U.S. Pat. No. 7,057,026, the disclosures of which are incorporated herein by reference in their entireties. The availability of fluorescently labeled terminators in which both the termination can be reversed and the fluorescent label cleaved facilitates efficient cyclic reversible termination (CRT) sequencing. Polymerases can also be co-engineered efficiently incorporate and extend from these modified nucleotides.

Alternatively, pyrosequencing techniques may be employed. Pyrosequencing detects the release of inorganic pyrophosphate (PPi) as particular nucleotides are incorporated into the nascent strand (Ronaghi et al., (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568; and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

Additional exemplary sequencing-by-synthesis methods that can be used with the methods described herein include those described in U.S. Patent Publication Nos. 2007/0166705, 2006/0188901; 2006/0240439; 2006/0281109, 2005/0100900; U.S. Pat. No. 7,057,026; WO 05/065814; WO 06/064199; WO 07/010251, the disclosures of which are incorporated herein by reference in their entireties.

Alternatively, sequencing by ligation techniques are used. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Other suitable alternative techniques include, for example, fluorescent in situ sequencing (FISSEQ), and Massively Parallel Signature Sequencing (MPSS).

Apparatus
Flow Cell Design

Various library capture devices may be provided with electrodes as described herein. Flow cells can serve as such devices. In various embodiments, the devices herein include one or more substrates upon which the nucleic acids to be sequenced are bound, attached or associated. See, e.g., WO 9844151 or WO0246456. In certain embodiments, a library sequencing region is within a channel or other area as part of a "flow cell." The flow cells used in the various embodiments can include millions of individual nucleic acid clusters, e.g., about 2-8 million clusters per channel. Each of such clusters can give read lengths of at least 25 bases for DNA sequencing and 20 bases for gene expression analysis. In certain embodiments, the flow cells herein can generate a gigabase (one billion bases) of sequence per run (e.g., 5 million nucleic acid clusters per channel, 8 channels per flow cell, 25 bases per polynucleotide).

Figure 13A:
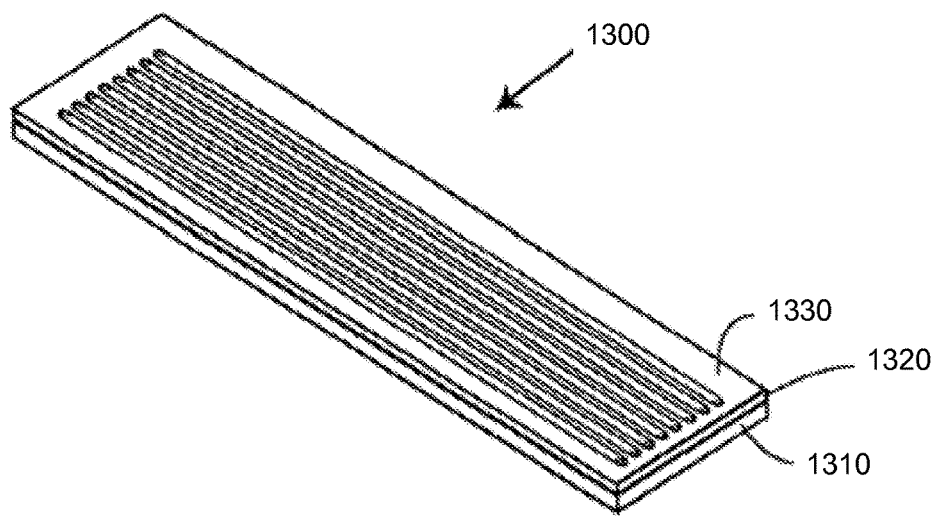
FIGS. 13A and 13B display an exemplary embodiment of a flow cell.
Figure 13B:
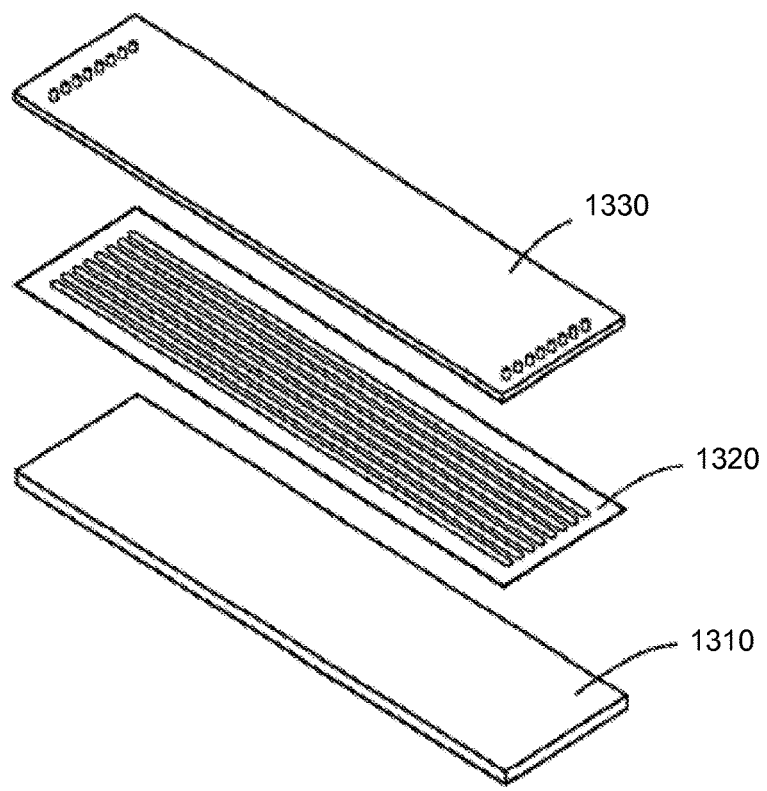

FIGS. 13A and 13B display one exemplary embodiment of a flow cell. As can be seen, the particular flow cell embodiment, flow cell 1300, includes a base layer 1310 (e.g., of borosilicate glass 1000 um in depth), channel layer 1320 (e.g., of etched silicon 100 um in depth) overlaid upon the base layer, and cover, or top, layer 1330 (e.g., 300 um in depth). When the layers are assembled together, enclosed channels are formed having inlet/outlets at either end through the cover. As will be apparent from the description of additional embodiments below, some flow cells include openings for the channels on the bottom.

The channeled layer can optionally be constructed using standard photolithographic methods, with which those of skill in the art will be familiar. One such method, which can be used in some embodiments, involves exposing a 100 um layer of silicon and etching away the exposed channel using Deep Reactive Ion Etching or wet etching.

Figure 13C:
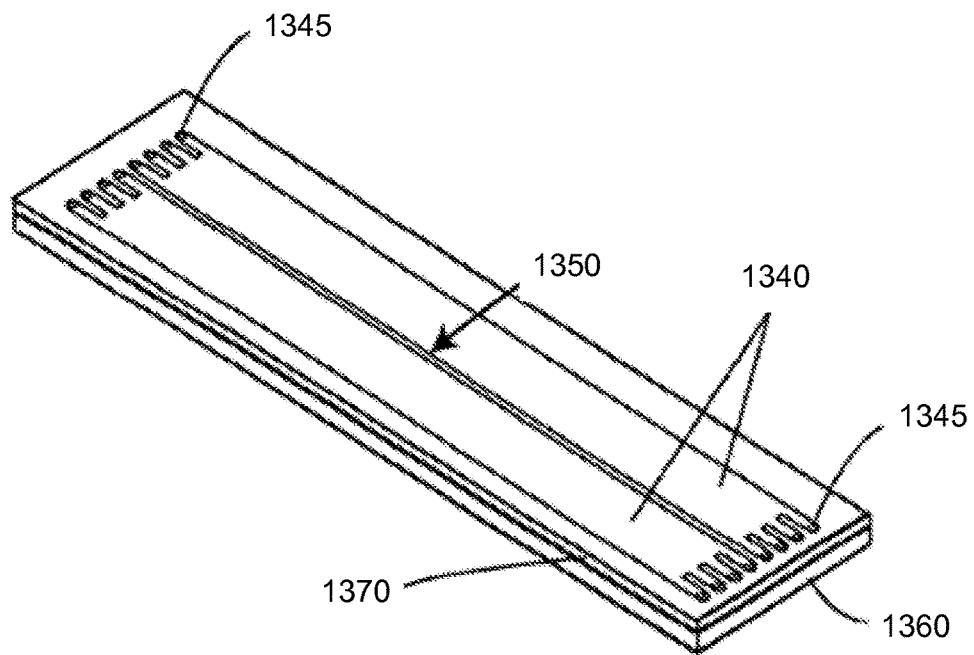
FIGS. 13C and 13D display additional exemplary flow cell designs.
Figure 13D:
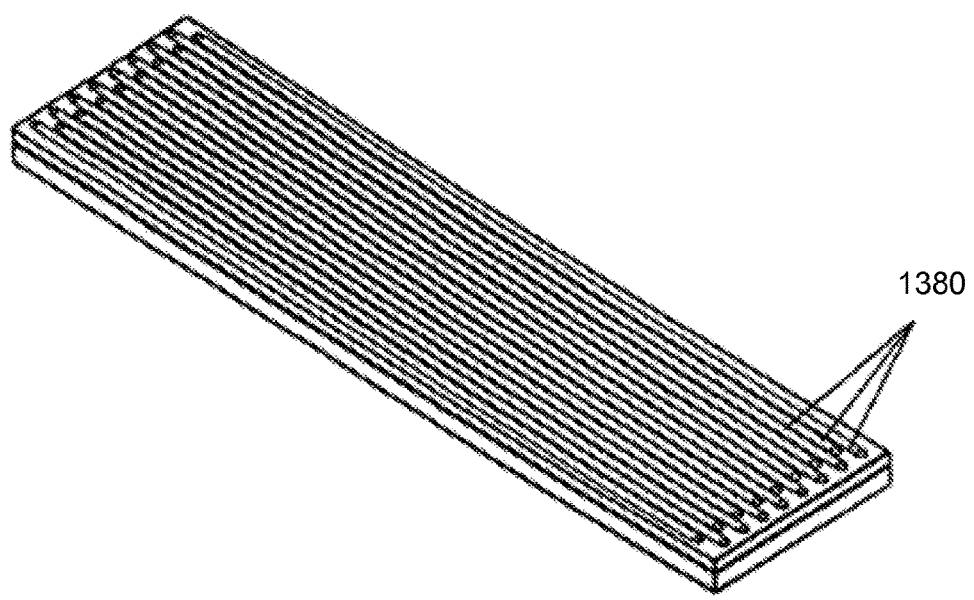

It will be appreciated that while particular flow cell configurations are presented herein, such configurations should not be taken as limiting. Thus, for example, various flow cells herein can include different numbers of channels (e.g., 1 channel, 2 or more channels, 4 or more channels, or 6, 8, 10, 16 or more channels, etc. Additionally, various flow cells can include channels of different depths and/or widths (different both between channels in different flow cells and different between channels within the same flow cell). For example, while the channels formed in the cell in FIG. 13B are 100 um deep, other embodiments can optionally comprise channels of greater depth (e.g., 500 um) or lesser depth (e.g., 50 um). Additional exemplary flow cell designs are shown in FIGS. 13C and 13D (e.g., a flow cell with "wide" channels, such as channels 1340 in FIG. 13C, having two channels with 8 inlet and outlet ports (ports 1345—8 inlet and 8 outlet) to maintain flow uniformity and a center wall, such as wall 1350, for added structural support; or a flow cell with offset channels, such as the 16 offset channels (channels 1380), etc.). The flow cells can be designed to maximize the collection of fluorescence from the illuminated surface and obtain diffraction limited imaging. For example, in the design shown in FIG. 13C, in particular embodiments, the light comes into the channel through 1000 um thick bottom layer 1360, which can be made of borosilicate glass, fused silica or other material as described herein, and the emitted light travels through 100 um depth of aqueous solution within the channel and 300 um depth of "top" layer material 1370. However, in some embodiments, the thickness of the "top" layer may be less than 300 um to prevent spherical aberrations and to image a diffraction limited spot. For example the thickness of the top layer can be around 170 um for use with a standard diffraction limited optical system. To use the thicker top layer without suffering from spherical aberrations, the objective can optionally be custom designed, e.g., as described herein.

In the various embodiments herein, the flow cells can be created from/with a number of possible materials. For example, in some embodiments, the flow cells can comprise photosensitive glass(es) such as Foturan® (Mikroglas, Mainz, Germany) or Fotoform® (Hoya, Tokyo, Japan) that can be formed and manipulated as necessary. Other possible materials can include plastics such as cyclic olefin copolymers (e.g., Topas® (Ticona, Florence, Ky.) or Zeonor® (Zeon Chemicals, Louisville, Ky.)) which have excellent optical properties and can withstand elevated temperatures if need be (e.g., up to 100° C.). As will be apparent from FIG. 4, the flow cells can comprise a number of different materials within the same cell. Thus, in some embodiments, the base layer, the walls of the channels, and the top/cover layer can optionally be of different materials.

While the example in FIG. 13B shows a flow cell containing 3 layers, other embodiments can include 2 layers, e.g., a base layer having channels etched/ablated/formed within it and a top cover layer, etc. Additionally, other embodiments provide flow cells having only one layer which contains the flow channel etched/ablated/otherwise formed within it.

In some embodiments, the flow cells are constructed from Foturan®. Foturan is a photosensitive glass which can be structured for a variety of purposes. It combines various desired glass properties (e.g., transparency, hardness, chemical and thermal resistance, etc.) and the ability to achieve very fine structures with tight tolerances and high aspect ratios (hole depth/hole width). With Foturan® the smallest structures possible are usually, e.g., 25 um with a roughness of 1 um.

Figure 6:
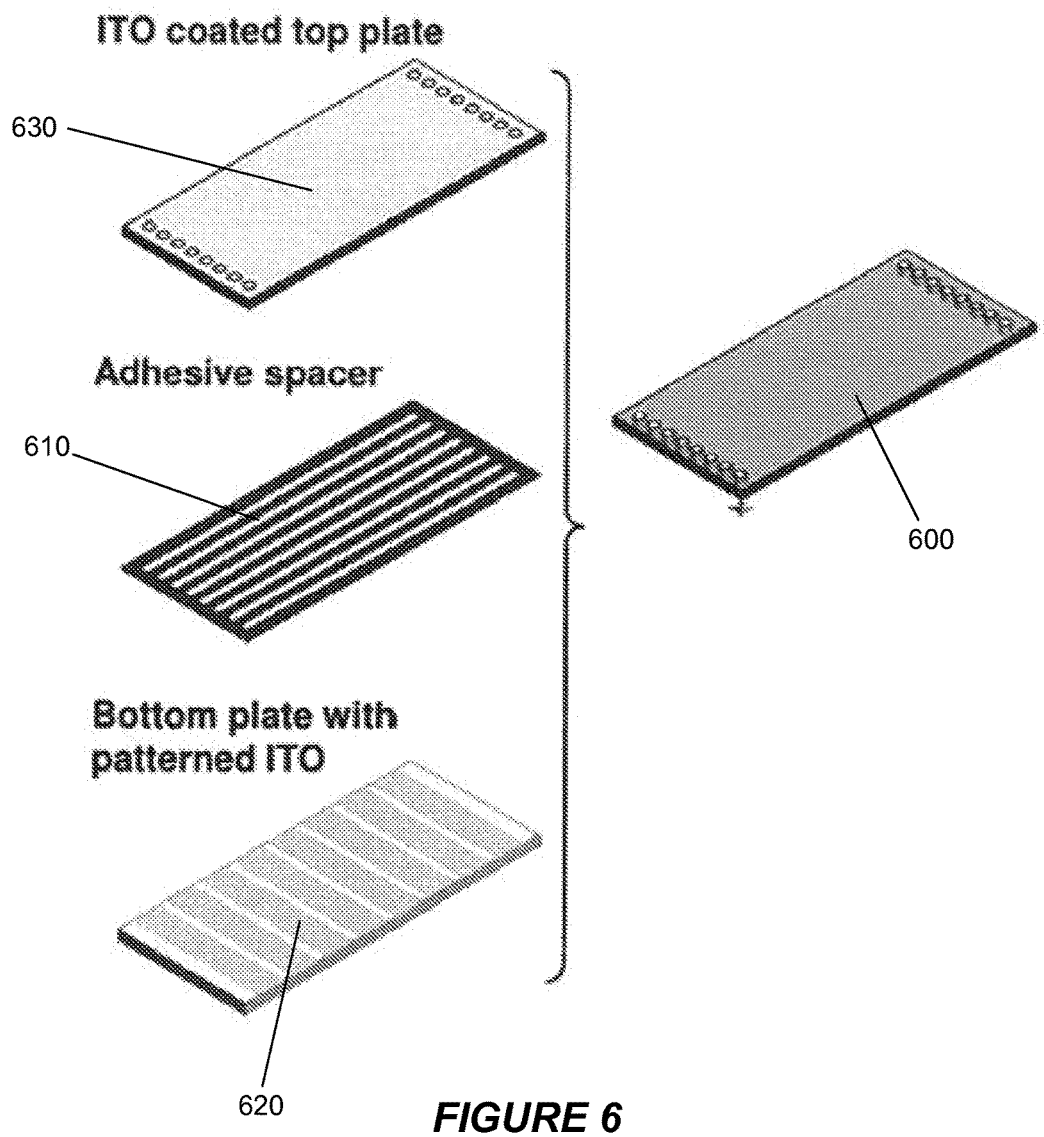
FIG. 6 is an exploded view of a flow cell having eight lanes and eight electrodes disposed along the bottom plate of the flow cell, in accordance with some implementations.

FIG. 6 depicts how the flow cell design may be modified to include ITO electrodes on the bottom plate 620, and an ITO coated top plate 630. The bottom plate 620 may be patterned to include segments of ITO electrodes, so that a given lane of a flow cell may include 6-12 electrodes, each separately activatable. During capture, the top plate 630 may be held at a single potential while the lower electrodes are held at different potentials. For example, when a bottom electrode is held at about +0.6V, the top plate is held at about −0.3V to repel polynucleotides, pushing them toward the bottom plate 620 and the positively charged electrode(s).

In some embodiments, the electrodes of the flow cell may be arranged parallel to one another and perpendicular to the lanes of the flow cell. Some embodiments of the flow cell may include six to twelve rectangular electrodes disposed in parallel along the flow cell. Electrodes may be embedded in flow cells having various dimensions, including dimensions used in current Illumina® GA®, MiSeq®, HiSeq® platforms and others. The dimensions of the flow cell may vary as long as the flow cell can successfully interface with existing and future sequencing platforms.

Figure 14:
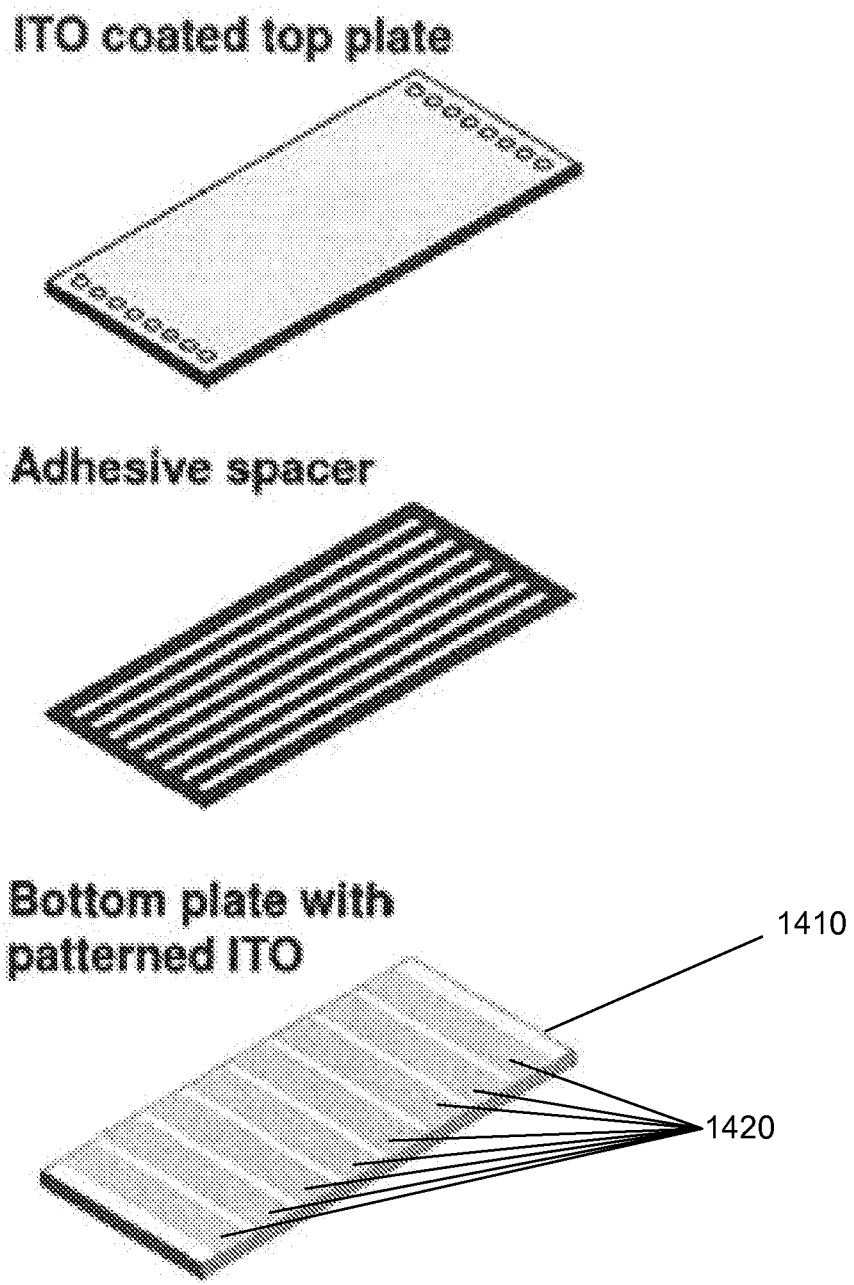
FIG. 14 is an exploded view of a flow cell having eight lanes and eight electrodes disposed along the bottom plate of the flow cell.

FIG. 14 is an exploded view of a flow cell having eight lanes and eight electrodes disposed along the bottom plate of the flow cell. FIG. 14 depicts this configuration for electrodes in a flow cell. In this embodiment, eight electrodes are placed in parallel along the bottom plate 1410 of the flow cell, and the electrodes 1420 run perpendicular to the lanes of the flow cell. This effectively partitions each lane of the flow cell into eight sections, allowing for eight different libraries to be sequenced on a single lane of the flow cell. In a flow cell having eight lanes, the flow cell may be used to sequence up to 64 different polynucleotide libraries.

Figure 15A:
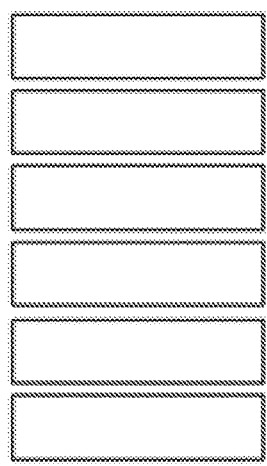
FIG. 15A shows a planar view of two possible configurations of electrodes on a flow cell.
Figure 15A:
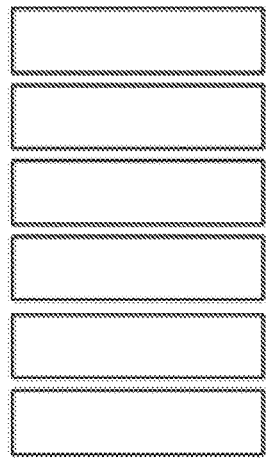
Figure 15B:
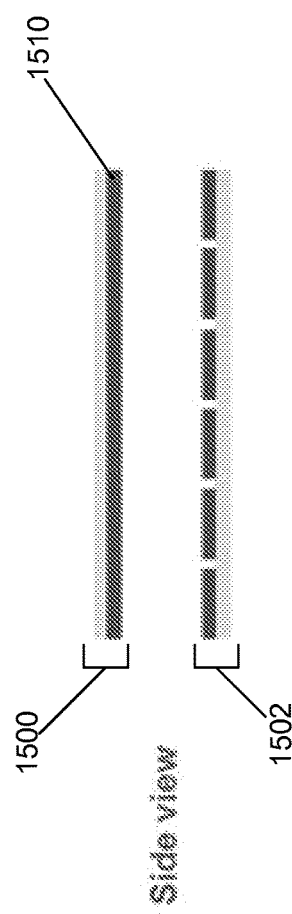
FIG. 15B shows a side view of two possible configurations of electrodes on a flow cell.
Figure 15B:
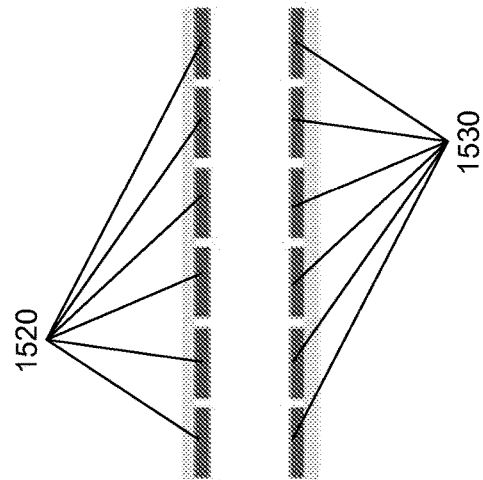

FIGS. 15A and 15B depict alternative electrode designs for a flow cell. FIG. 15A shows a planar view of two possible configurations of electrodes on a flow cell. FIG. 15B shows a side view of two possible configurations of electrodes on a flow cell. As FIG. 15B demonstrates, the upper plate 1500 may be patterned with ITO either as a single electrode 1510 across the entire upper plate 1500, or as counter electrodes 1520 that match the electrodes 1530 on the bottom plate 1502. When one of the bottom plate electrodes is positively charged, the upper plate 1500 may be held at a negative voltage to further push polynucleotides away from the top plate 1500 toward the amplification primers on the bottom plate 1502. In other embodiments, the counter electrodes may reside outside of the flow cell surface, for example, at the inlet and outlets of the flow cell lanes or on the outside surface of the upper plate.

Fabrication of Flow Cells With Electrodes

In some embodiments, electrodes can be fabricated on top and bottom flow cell surfaces using standard micro-fabrication techniques prior to flow cell assembly. For example, gold electrodes can be patterned by lift-off photolithography; and ITO electrodes can be patterned by photolithography and wet etching or laser ablation.

Figure 16A:
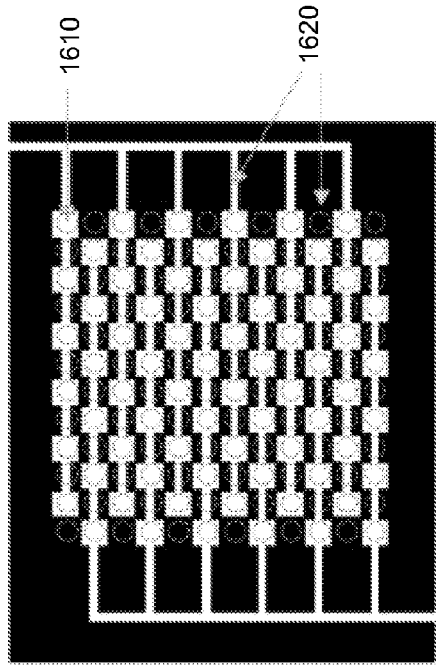
FIGS. 16A and 16B show an example of a design where the gold electrodes are partially covered and passivated by silicon nitride.
Figure 16B:
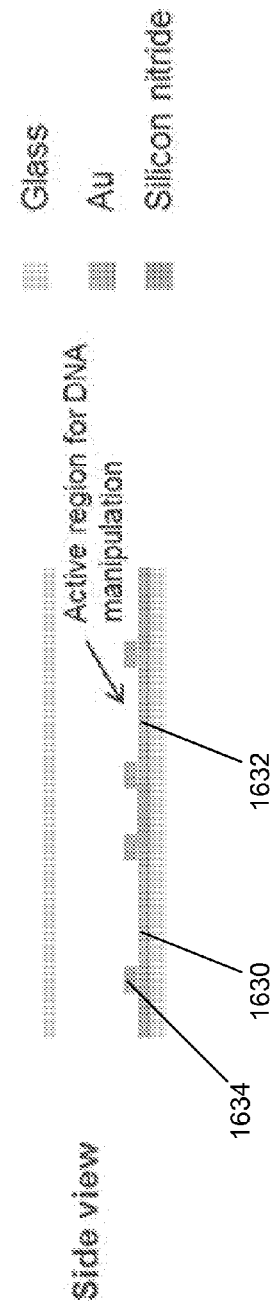

FIGS. 16A and 16B show an example of a design where the gold electrodes are partially covered and passivated by silicon nitride, so that the active region for DNA manipulation is concentrated in the areas where the gold electrode is exposed. Silicon nitride, or any similar compound may be deposited on the flow cell to create areas of active DNA manipulation and areas where the electrodes are not exposed. FIG. 16A shows a planar view of such a design, in which the white circles represent exposed gold electrodes, and the black circles 1620 represent electrodes that are passivated with nitrides. In one implementation, the exposed gold electrodes 1610 may be 20 um in diameter and spaced apart from each other by 10 um. FIG. 16B shows a side view of a flow cell containing two gold electrodes 1630, 1632 and deposits of silicon nitride 1634.

A polymer attachment layer anchors the amplification primers or other capture moieties to the library capture surface of a flow cell. A polymer attachment layer composed of silane-free acrylamide (SFA) may be directly deposited on Au and ITO electrodes without any chemical modifications of the electrodes. A polymer attachment comparable to poly(N-(5-azidoacetamidylpentyl)acrylamide-co-acrylamide) (PAZAM) may be attached to silanized ITO electrodes.

One type of polymer attachment layer employs a hydrogel. In preparing hydrogel-based solid-supported molecular arrays, a hydrogel is formed and molecules displayed from it. These two features—formation of the hydrogel and construction of the array—may be effected sequentially or simultaneously. Where the hydrogel is formed prior to formation of the array, it is typically produced by allowing a mixture of co-monomers to polymerize. Generally, the mixture of co-monomers contain acrylamide and one or more co-monomers, the latter of which permit, in part, subsequent immobilization of molecules of interest so as to form the molecular array.

The co-monomers used to create the hydrogel typically contain a functionality that serves to participate in cross-linking of the hydrogel and/or immobilize the hydrogel to the solid support and facilitate association with the target molecules of interest.

Clustered arrays may be formed on such solid-supported hydrogels by solid phase nucleic acid amplification using forward and reverse amplification primers attached to the hydrogel at their 5' ends, leading to the production of clustered arrays of amplification products having the "bridged" structure. In order to maximize the efficiency of sequencing reactions using templates derived from such bridged products there is a need for linearization methods which are compatible with the hydrogel surface and with subsequent nucleic acid sequencing reactions.

WO 00/31148 discloses polyacrylamide hydrogels and polyacrylamide hydrogel-based arrays in which a so-called polyacrylamide prepolymer is formed, optionally from acrylamide and an acrylic acid or an acrylic acid derivative containing a vinyl group. Crosslinking of the prepolymer may then be effected. The hydrogels so produced are solid-supported, preferably on glass. Functionalization of the solid-supported hydrogel may also be effected.

WO 01/01143 describes technology similar to WO 00/31148 but differing in that the hydrogel bears functionality capable of participating in a [2+2] photocycloaddition reaction with a biomolecule so as to form immobilized arrays of such biomolecules. Dimethylmaleimide (DMI) is a particularly preferred functionality. The use of [2+2] photocycloaddition reactions, in the context of polyacrylamide-based microarray technology is also described in WO02/12566 and WO03/014392.

U.S. Pat. No. 6,465,178 discloses the use of reagent compositions in providing activated slides for use in preparing microarrays of nucleic acids; the reagent compositions include acrylamide copolymers. The activated slides are stated to be particularly well suited to replace conventional (e.g. silylated) glass slides in the preparation of microarrays.

WO00/53812 discloses the preparation of polyacrylamide-based hydrogel arrays of DNA and the use of these arrays in replica amplification.

The solid upon which the hydrogel is supported is not limited to a particular matrix or substrate. Indeed, this is one of the advantages of these embodiments: the same chemistry used to modify silica-based substrates can be applied to other solid supports and allows the solid support to be adapted to suit any particular application to which it is desired to be put rather than being constrained by the surface chemistry it is possible to perform on any given support. Solids which may be of use in the practice of the disclosed embodiments thus include silica-based substrates, such as glass, fused silica and other silica-containing materials; they may also be silicone hydrides or plastic materials such as polyethylene, polystyrene, poly(vinyl chloride), polypropylene, nylons, polyesters, polycarbonates and poly(methyl methacrylate). Example plastics material are poly(methyl methacrylate), polystyrene and cyclic olefin polymer substrates. Alternatively, other solid supports may be used such as gold, titanium dioxide, or silicon supports. The foregoing lists are intended to be illustrative of, but not limited to, the disclosed embodiments. In certain embodiments, the support is a silica-based material or plastic material such as discussed herein.

Plastics-based substrates for molecular arrays may be relatively inexpensive: the preparation of appropriate plastics-based substrates by, for example injection-molding, is generally cheaper than the preparation, e.g. by etching and bonding, of silica-based substrates. Another advantage is the nearly limitless variety of plastics allowing fine-tuning of the optical properties of the support to suit the application for which it is intended or to which it may be put.

In certain embodiments, the support is silica-based but the shape of the support employed may be varied in accordance with the application for which the disclosed embodiments are practiced. Generally, however, slides of support material, such as silica, e.g. fused silica, are of particular utility in the preparation and subsequent integration of molecules. Of particular use in the practice of the disclosed embodiments are fused silica slides sold under the trade name SPECTRA-SIL™. This notwithstanding, it will be evident to the skilled person that the disclosed embodiments are equally applicable to other presentations of solid support (including silica-based supports), such as beads, rods and the like.

Sequencing Systems

While total internal reflection microscopy has been used to image both single and amplified molecules of DNA on surfaces, a robust, reliable, four color DNA sequencing platform (e.g., comprising heating systems, fluidic controls, uniform illumination, control of the optical beam shape, an autofocus system, and full software control of all components) is described herein.

The disclosed systems and devices may be used to analyze a large number of different nucleic acid sequences from, e.g., clonally amplified single-molecule DNA arrays in flow cells, or from an array of immobilized beads. In particular, the systems and devices utilize electrode arrays configured to capture DNA libraries when a positive bias is applied, isolating DNA from different samples to different regions of a flow cell for multiplexed sequencing. The systems herein are optionally useful in, e.g., sequencing for comparative genomics (such as for genotyping, SNP discovery, BAC-end sequencing, chromosome breakpoint mapping, and whole genome sequence assembly), tracking gene expression, micro RNA sequence analysis, epigenomics (e.g., with methylation mapping DNAsel hypersensitive site mapping or chromatin immunoprecipitation), and aptamer and phage display library characterization. Of course, those of skill in the art will readily appreciate that the disclosed embodiments are also amenable to use for myriad other sequencing applications.

Figure 17:
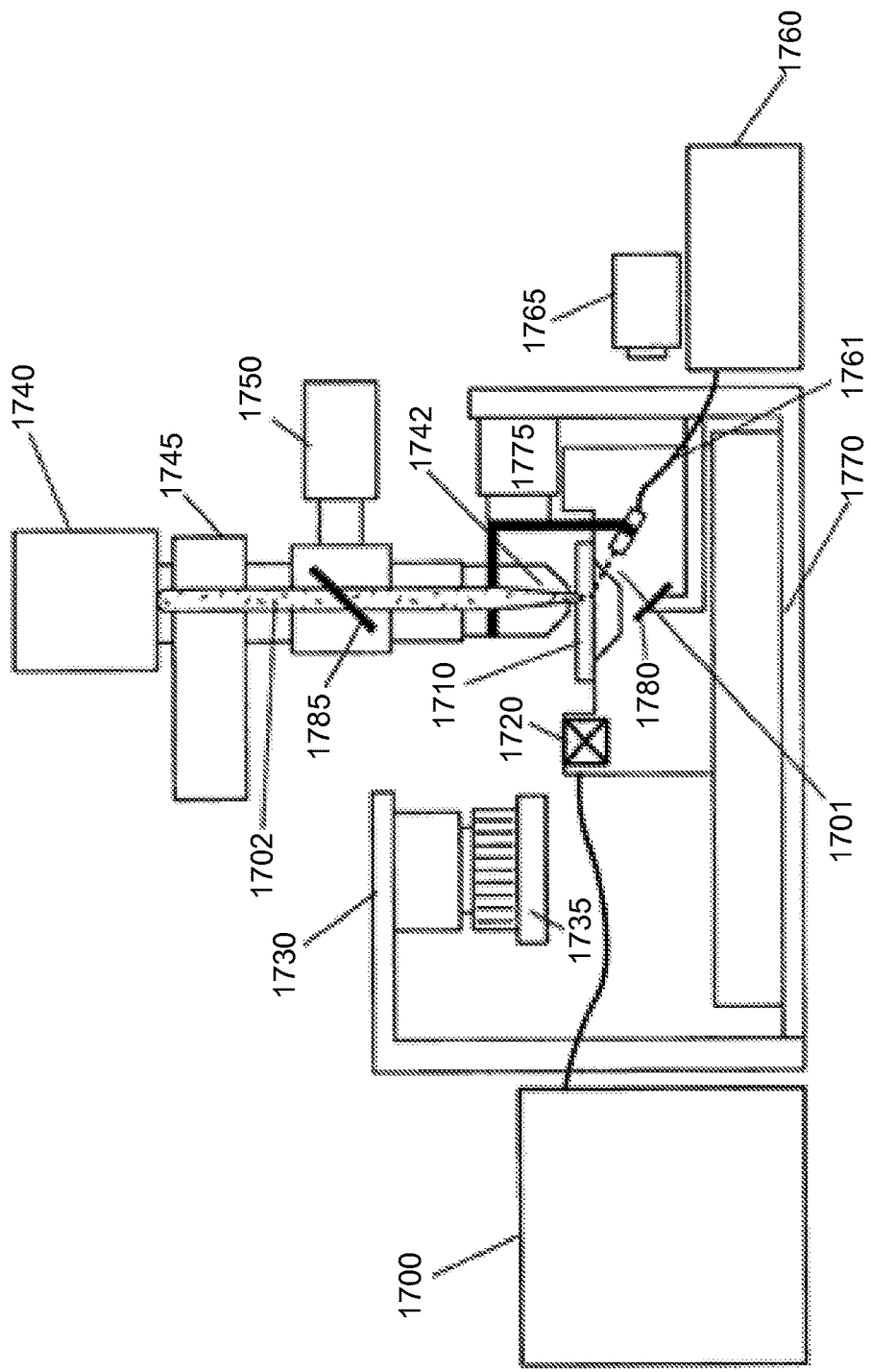
FIG. 17 shows an exemplary TIRF imaging configuration of a backlight design embodiment of a sequencing system.

An illustrative embodiment is outlined in FIG. 17, which shows an exemplary TIRF imaging configuration of a backlight design embodiment. As can be seen in FIG. 17, fluid delivery module or device 1700 directs the flow of reagents (e.g., fluorescent nucleotides, buffers, enzymes, cleavage reagents, etc.) to (and through) flow cell 1710 and waste valve 1720. In particular embodiments, the flow cell comprises clusters of nucleic acid sequences (e.g., of about 200-1000 bases in length) to be sequenced which are optionally attached to the substrate of the flow cell, as well as optionally other components. The flow cell can also comprise an array of beads, where each bead optionally contains multiple copies of a single sequence. The preparation of such beads can be performed according to a variety of techniques, for example as described in U.S. Pat. No. 6,172,218 or WO04069849 (Bead emulsion nucleic acid amplification).

The system also comprises temperature station actuator 1730 and heater/cooler 1735, which can optionally regulate the temperature of conditions of the fluids within the flow cell. As explained below, various embodiments can comprise different configurations of the heating/cooling components. The flow cell is monitored, and sequencing is tracked, by camera system 1740 (e.g., a CCD camera) which can interact with various filters within filter switching assembly 1745, lens objective 1742, and focusing laser/focusing laser assembly 1750. Laser device 1760 (e.g., an excitation laser within an assembly optionally comprising multiple lasers) acts to illuminate fluorescent sequencing reactions within the flow cell via laser illumination through fiber optic 1761 (which can optionally comprise one or more re-imaging lenses, a fiber optic mounting, etc. Low watt lamp 1765, mirror 1780 and reverse dichroic 1785 are also presented in the embodiment shown. See below. Additionally, mounting stage 1770, allows for proper alignment and movement of the flow cell, temperature actuator, camera, etc. in relation to the various components of the disclosed embodiments. Focus (z-axis) component 1775 can also aid in manipulation and positioning of various components (e.g., a lens objective). Such components are optionally organized upon a framework and/or enclosed within a housing structure. It will be appreciated that the illustrations herein are of exemplary embodiments and are not necessarily to be taken as limiting. Thus, for example, different embodiments can employ different placement of components relative to one another (e.g., embodiment A includes a heater/cooler as in FIG. 17, while embodiment B includes a heater/cooler component beneath its flow cell, etc.).

Figure 18:
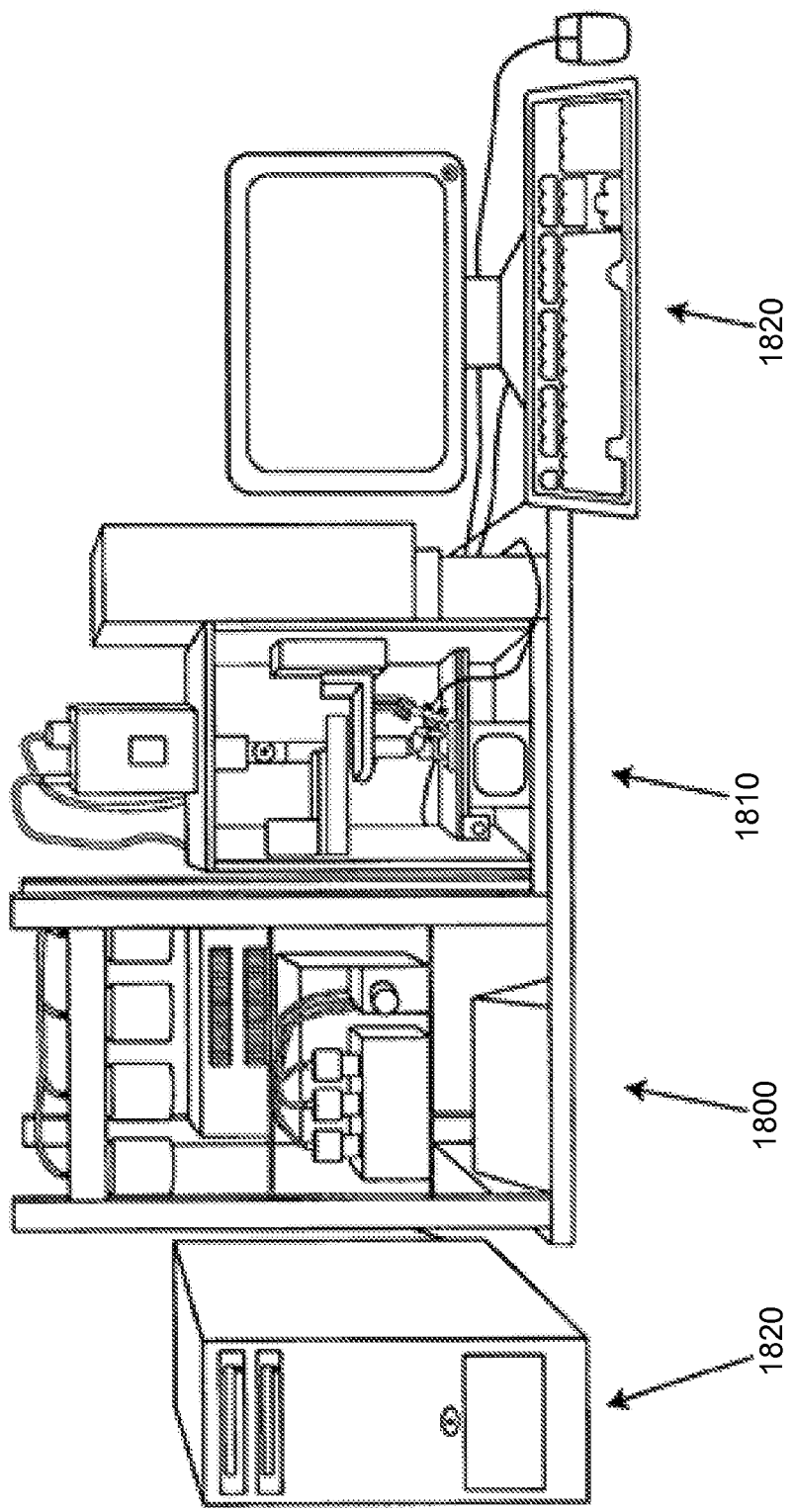
FIG. 18 shows an exemplary arrangement of a sequencing system of the disclosed embodiments.

FIG. 18 presents an exemplary arrangement of a system that may be used with electrode-containing flow cells as disclosed herein. As can be seen, the system can be divided into certain basic groupings, e.g., area 1800 comprising fluidics and reagent storage (including pumps and motors or the like for producing and regulating fluid flow, heaters/coolers for proper reagent temperatures, etc.), area 1810 comprising flow cell and detection (including one or more cameras or similar devices, one or more lasers or other light sources, one or more appropriate optical filters and lenses, a temperature control actuator, e.g., with Peltier heating/cooling for control of the temperature conditions of the flow cell, a movable staging platform and motors controlling such to correctly position the various devices/components within the system), and area 1820 containing a computer module (including memory and a user interface such as a display panel and keyboard, etc.).

As indicated above, the disclosed embodiments include systems and devices for sequencing nucleic acids. Sequencing of a target fragment means that a read of the chronological order of bases is established. The bases that are read do not need to be contiguous, although this is often the case, nor does every base on the entire fragment have to be sequenced during the sequencing. As explained, sequencing can be carried out using any suitable sequencing technique, where nucleotides or oligonucleotides are added successively to a free 3' hydroxyl group, resulting in synthesis of a polynucleotide chain in the 5' to 3' direction. The nature of the nucleotide added is typically determined after each nucleotide addition. Sequencing techniques using sequencing by ligation, wherein not every contiguous base is sequenced, and techniques such as massively parallel signature sequencing (MPSS) where bases are removed from, rather than added to, the strands on the surface are also amenable to use with the systems and devices such as depicted in FIGS. 17 and 18.

In particular uses of the systems/devices herein, the flow cells containing the nucleic acid samples for sequencing are placed within the appropriate flow cell holder of the disclosed embodiments. The samples for sequencing can take the form of single molecules, amplified single molecules in the form of clusters, or beads comprising molecules of nucleic acid. The nucleic acids are prepared such that they comprise an oligonucleotide primer adjacent to an unknown target sequence. To initiate the first SBS sequencing cycle, one or more differently labeled nucleotides, and DNA polymerase, etc., are flowed into/through the flow cell by the fluid flow subsystem (various embodiments of which are described herein). Either a single nucleotide can be added at a time, or the nucleotides used in the sequencing procedure can be specially designed to possess a reversible termination property, thus allowing each cycle of the sequencing reaction to occur simultaneously in the presence of all four labeled nucleotides (A, C, T, G). Where the four nucleotides are mixed together, the polymerase is able to select the correct base to incorporate and each sequence is extended by a single base. In such methods of using the systems of the disclosed embodiments, the natural competition between all four alternatives leads to higher accuracy than wherein only one nucleotide is present in the reaction mixture (where most of the sequences are therefore not exposed to the correct nucleotide). Sequences where a particular base is repeated one after another (e.g., homopolymers) are addressed like any other sequence and with high accuracy.

Fluid Flow

The fluid flow subsystem also flows the appropriate reagents to remove the blocked 3' terminus (if appropriate) and the fluorophore from each incorporated base. The substrate can be exposed either to a second round of the four blocked nucleotides, or optionally to a second round with a different individual nucleotide. Such cycles are then repeated and the sequence of each cluster is read over the multiple chemistry cycles. The computer aspect of the disclosed embodiments can optionally align the sequence data gathered from each single molecule, cluster or bead to determine the sequence of longer polymers, etc. Alternatively, the image processing and alignment can be performed on a separate computer.

Figure 19A:
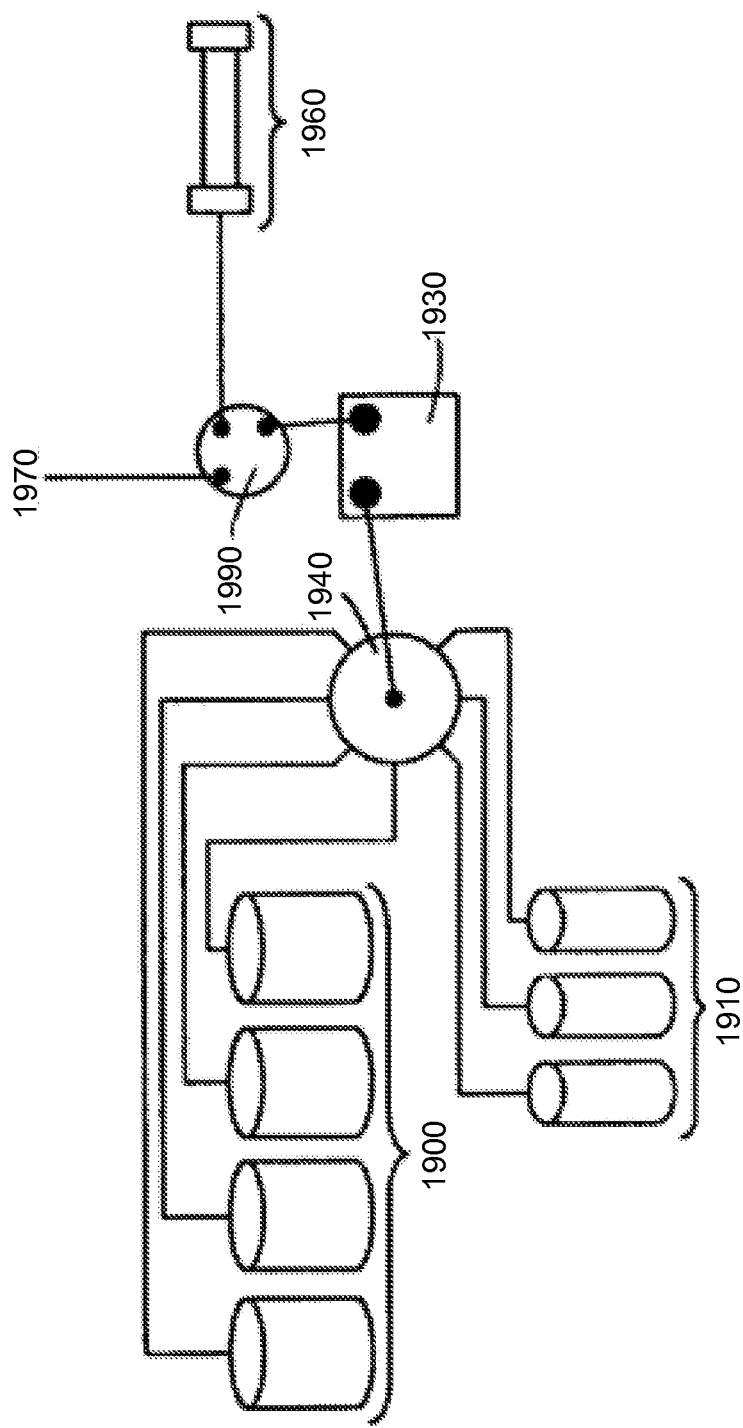
FIGS. 19A-C present generalized diagrams of exemplary fluid flow arrangements of some embodiments.
Figure 19B:
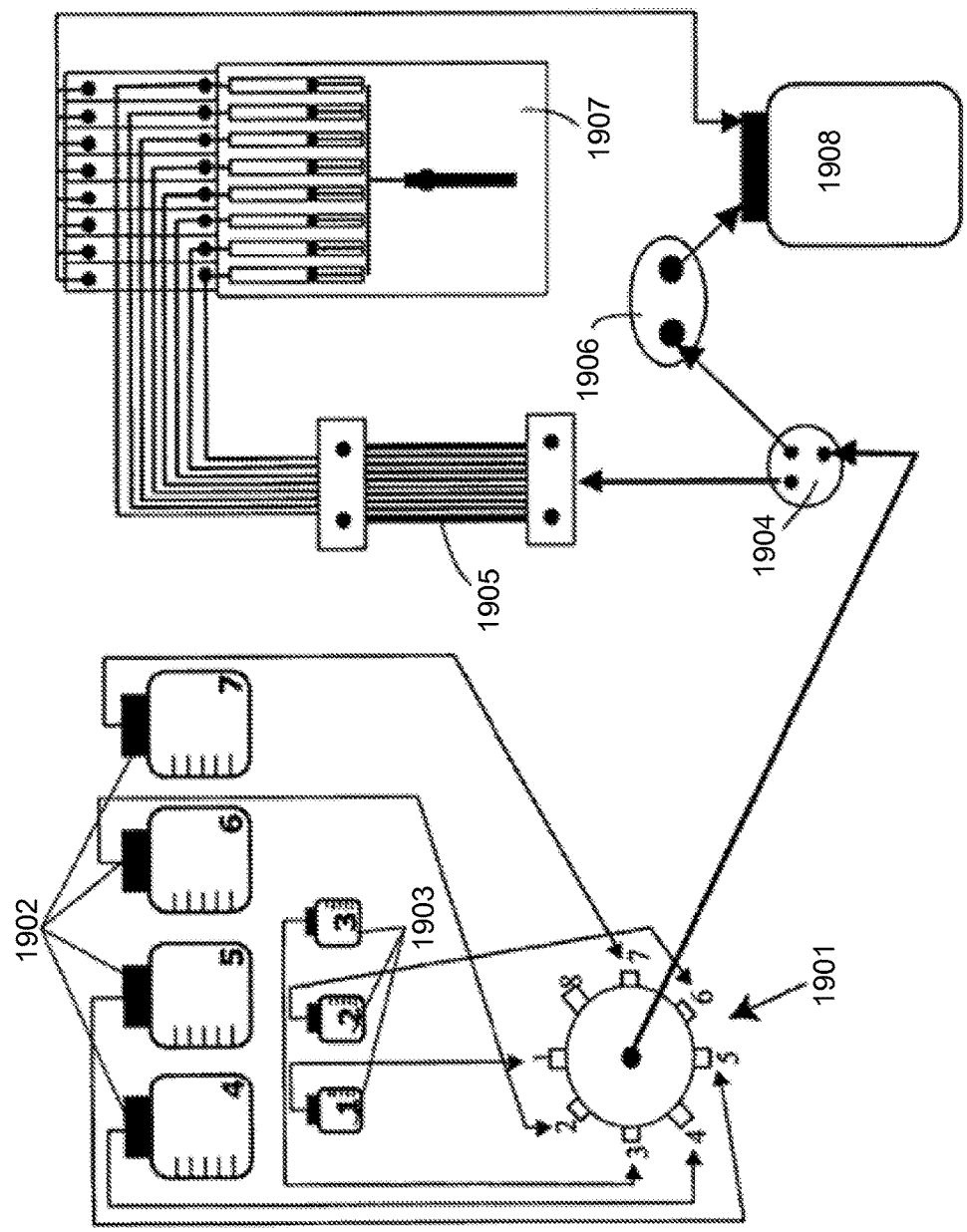
Figure 19C:
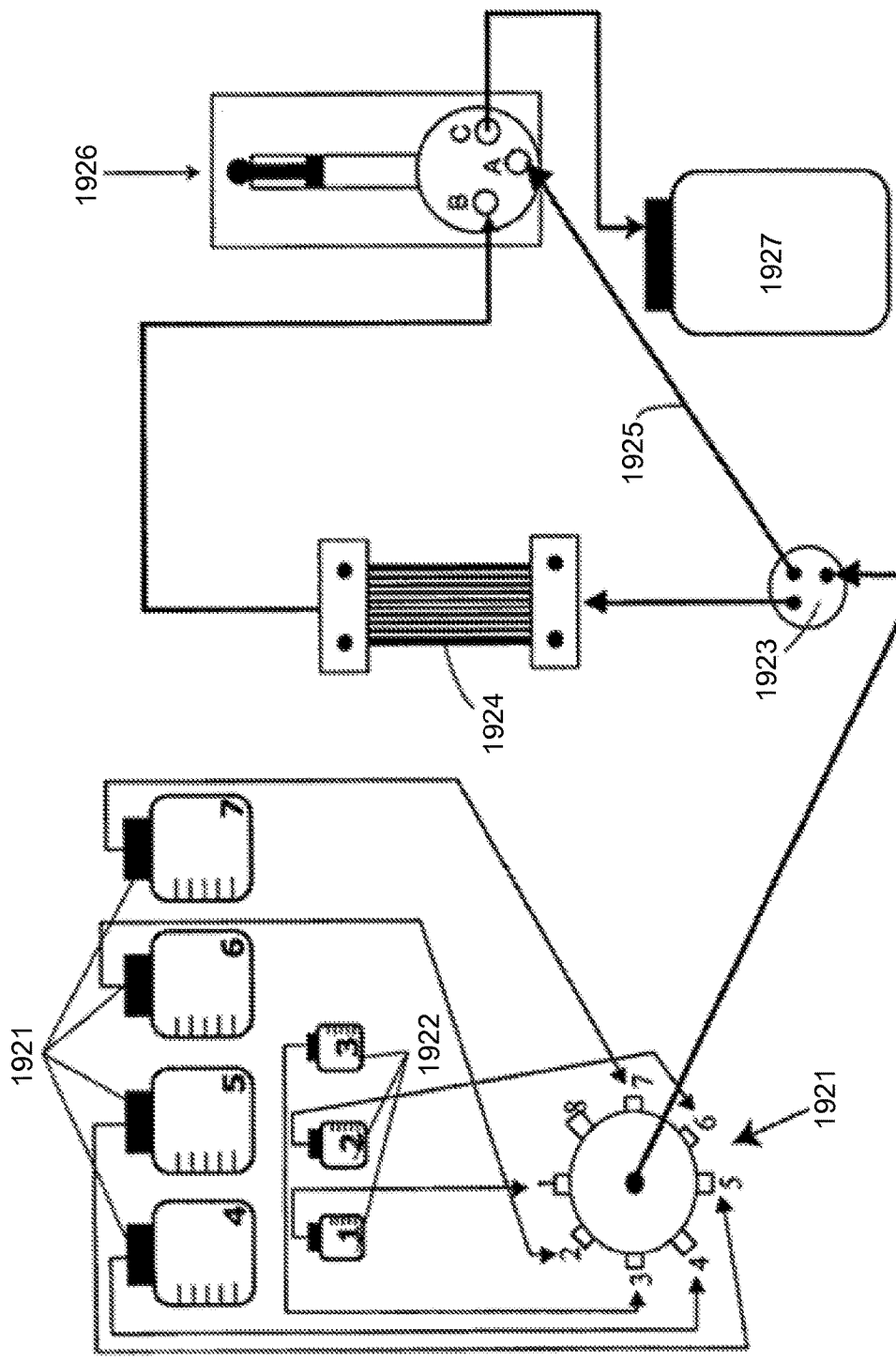

In the various embodiments herein, the reagents, buffers, etc. used in the sequencing of the nucleic acids are regulated and dispensed via a fluid flow subsystem or aspect. FIGS. 19A-C present generalized diagrams of exemplary fluid flow arrangements of the disclosed embodiments, set up in one way push, eight way pull, and one way pull configurations respectively. In general, the fluid flow subsystem transports the appropriate reagents (e.g., enzymes, buffers, dyes, nucleotides, etc.) at the appropriate rate and optionally at the appropriate temperature, from reagent storage areas (e.g., bottles, or other storage containers) through the flow cell and optionally to a waste receiving area.

The fluid flow aspect is optionally computer controlled and can optionally control the temperature of the various reagent components. For example, certain components are optionally held at cooled temperatures such as $4°$ C.$+1-1°$ C. (e.g., for enzyme containing solutions), while other reagents are optionally held at elevated temperatures (e.g., buffers to be flowed through the flow cell when a particular enzymatic reaction is occurring at the elevated temperature).

In some embodiments, various solutions are optionally mixed prior to flow through the flow cell (e.g., a concentrated buffer mixed with a diluent, appropriate nucleotides, etc.). Such mixing and regulation is also optionally controlled by the fluid flow aspect of the disclosed embodiments. It is advantageous if the distance between the mixed fluids and the flow cell is minimized in many embodiments. Therefore the pump can be placed after the flow cell and used to pull the reagents into the flow cell (FIGS. 19B and 19C) as opposed to having the pump push the reagents into the flow cell (as in FIG. 19A). Such pull configurations mean that any materials trapped in dead volumes within the pump do not contaminate the flow cell. The pump can be a syringe type pump, and can be configured to have one syringe per flow channel to ensure even flow through each channel of the flow cell. The pump can be an 8 way pump, if it is desired to use an 8 way flow cell, such as for example a Kloehn 8 way syringe pump (Kloehn, Las Vegas, Nev.). A fluidics diagram of an 8 way pull configuration is shown in FIG. 16B. In FIG. 16A, fluidic reagents are stored in reagent containers 1900 (e.g., buffers at room temperature, 5×SSC buffer, enzymology buffer, water, cleavage buffer, etc.) and 1910 (e.g., cooled containers for enzymes, enzyme mixes, water, scanning mix, etc.). Pump 1930 moves the fluids from the reagent containers through reagent valve 1940, priming/waste valve 1970 and into/through flow cell 1960.

In FIG. 19B, fluidic reagents are stored in reagent containers 1902 (e.g., buffers at room temperature similar to those listed above) and 1903 (e.g., cooled containers for enzymes, etc. similar to those listed above), linked through reagent valve 1901. Those of skill in the art will be familiar with multi-way valves (such as the reagent valves) used to allow controllable access of/to multiple lines/containers. The reagent valve is linked into flow cell 1905 via an optional priming valve (or waste valve) 1904, connected to optional priming pump 1906. The priming pump can optionally draw reagents from the containers up through the tubing so that the reagents are "ready to go" into the flow cell. Thus, dead air, reagents at the wrong temperature (e.g., because of sitting in tubing), etc. will be avoided. When the priming pump is drawing, the outflow is shunted into the waste area. During non-priming use, the reagents can be pulled through the flow cell using 8 channel pump 1907, which is connect to waste reservoir 1908.

In either embodiment (push or pull), the fluidic configurations can comprise "sipper" tubes or the like that extend into the various reagent containers in order to extract the reagents from the containers. FIG. 19C shows a single channel pump rather than an 8 channel pump. Single channel pump 1926 can also act as the optional priming pump, and thus optional priming pump or waste valve 1923 can be connected directly to pump 1926 through bypass 1925. The arrangement of components is similar in this embodiment as to that of FIG. 16B. Thus it comprises reagent containers 1921 and 1922, multi-way selector valve 1920, flow cell 1924, etc.

The fluid flow itself is optionally driven by any of a number of pump types, (e.g., positive/negative displacement, vacuum, peristaltic, etc.) such as an Encynova® 2-1 Pump (Encynova, Greeley, Colo.) or a Kloehn® V3 Syringe Pump (Kloehn, Las Vegas, Nev.). Again, it will be appreciated that specific recitation of particular pumps, etc. herein should not be taken as necessarily limiting and that various embodiments can comprise different pumps and/or pump types than those listed herein. In certain embodiments, the fluid delivery rate is from about 50 uL to about 500 uL/min (e.g., controlled +/−2 uL) for the 8 channels. In the 8 way pull configuration, the flow can be between 10-100 uL/min/channel, depending on the process. In some embodiments, the maximum volume of nucleotide reagents required for sequencing a polynucleotide of 25 bases is about 12 mL.

Whichever pump or pump type is used herein, the reagents are optionally transported from their storage areas to the flow cell through tubing. Such tubing, such as PTFE, can be chosen in order to, e.g., minimize interaction with the reagents. The diameter of the tubing can vary between embodiments (and/or optionally between different reagent storage areas), but can be chosen based on, e.g., the desire to decrease "dead volume" or the amount of fluid left in the lines; Furthermore, the size of the tubing can optionally vary from one area of a flow path to another. For example, the tube size from a reagent storage area can be of a different diameter than the size of the tube from the pump to the flow cell, etc.

The fluid flow subsystem of the disclosed embodiments also can control the flow rate of the reagents involved. The flow rate is optionally adjustable for each flow path (e.g., some flow paths can proceed at higher flow rates than others; flow rates can optionally be reversed; different channels can receive different reagent flows or different timings of reagent flows, etc.). The flow rate can be set in conjunction with the tube diameter for each flow path in order to have the proper volume of reagent, etc in the flow cell at a given time. For example, in some embodiments, the tubing through which the reagents flow is 0.3 mm ID, 0.5 mm, or 1.0 mm while the flow rate is 480 uL/min or 120 uL/min. In some embodiments, the speed of flow is optionally balanced to optimize the reactions of interest. High flow can cause efficient clearing of the lines and minimize the time spent in changing the reagents in a given flow cell volume, but can also cause a higher level of shear flow at the substrate surface and can cause a greater problem with leaks or bubbles. A typical flow rate for the introduction of reagents can be 15 uL/min/channel in some embodiments.

The system can be further equipped with pressure sensors that automatically detect and report features of the fluidic performance of the system, such as leaks, blockages and flow volumes. Such pressure or flow sensors can be useful in instrument maintenance and troubleshooting. The fluidic system can be controlled by the one or more computer component, e.g., as described below. It will be appreciated that the fluid flow configurations in the various embodiments of the disclosed embodiments can vary, e.g., in terms of number of reagent containers, tubing length/diameter/composition, types of selector valves and pumps, etc.

Heating/Cooling

The heating/cooling components of the system regulate the reaction conditions within the flow cell channels and reagent storage areas/containers (and optionally the camera, optics, and/or other components), while the fluid flow components allow the substrate surface to be exposed to suitable reagents for incorporation (e.g., the appropriate fluorescently labeled nucleotides to be incorporated) while unincorporated reagents are rinsed away. An optional movable stage upon which the flow cell is placed allows the flow cell to be brought into proper orientation for laser (or other light) excitation of the substrate and optionally .moved in relation to a lens objective to allow reading of different areas of the substrate. Additionally, other components of the system are also optionally movable/adjustable (e.g., the camera, the lens objective, the heater/cooler, etc.). During laser excitation, the image/location of emitted fluorescence from the nucleic acids on the substrate is captured by the camera component, thereby, recording the identity, in the computer component, of the first base for each single molecule, cluster or bead.

Microcontroller

The existing system may be modified to incorporate separate logic that controls activation of the different electrodes at different times, associated with delivery of different libraries to the flow cell. This may be performed by a microcontroller that interfaces with the flow cell and the sequencing system logic. The microcontroller could be utilized during capture of polynucleotides delivered into the flow cell. In another embodiment, the microcontroller may be embedded in the system itself.

Figure 20:
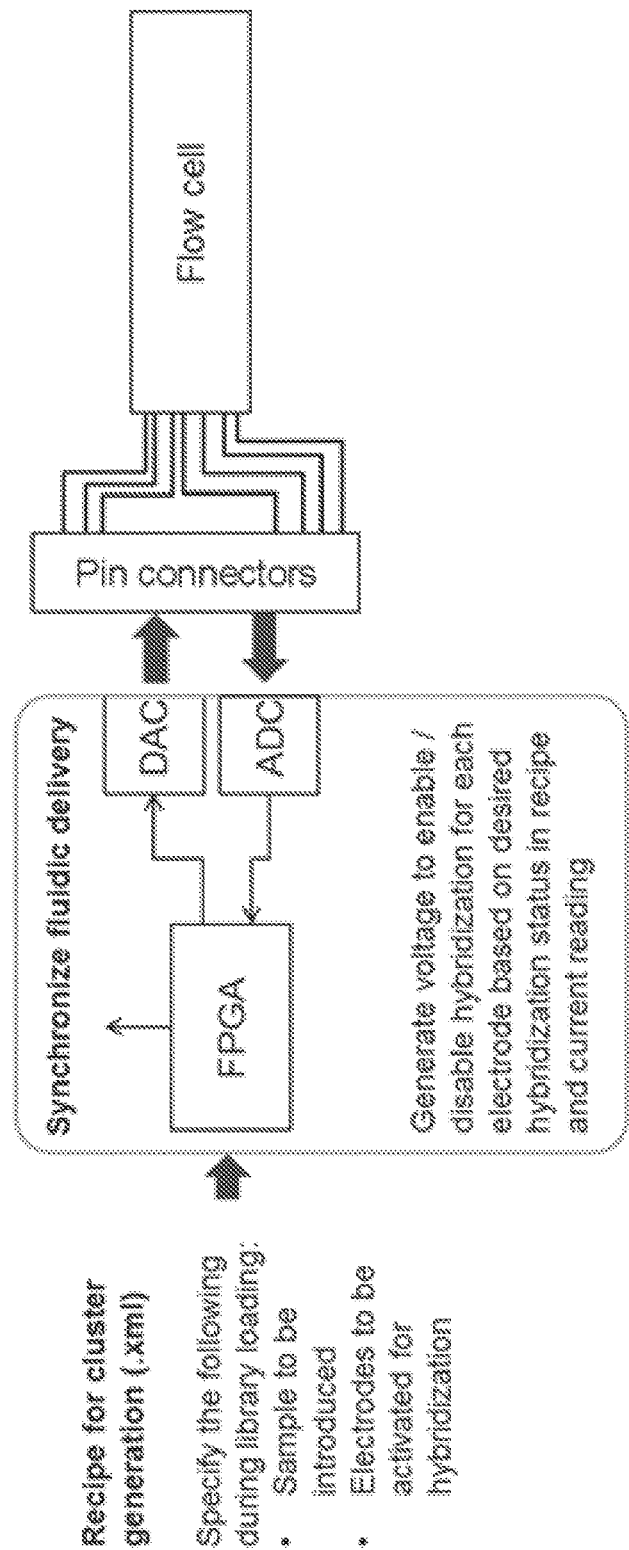
FIG. 20 shows how the electrodes of the flow cell may be interfaced with the sequencing system and controller.

FIG. 20 shows how the electrodes of the flow cell may be interfaced with the sequencing system and controller. In some embodiments, the recipe for cluster generation may include desired locations for hybridization, and extra hardware (FPGA, DAC, ADC) may be added to the controller board to read desired spatial hybridization statuses and control each electrode accordingly. In some embodiments, these features may be implemented on an Illumina® cBot®/MiSeq® controller board. The microcontroller may be designed or programmed to operate the electrodes in direct current (DC) or alternating current (AC) mode. In various embodiments, the controller synchronizes delivery of particular libraries (fluidically to a flow cell) with activation of certain electrodes in the library capture region.

EXAMPLES

Electrode Configuration: Interdigitated Electrode Configuration

In one example, electrodes were arranged such that interdigitated gold electrodes are arranged in parallel to each other. Multiple electrodes can be arranged in parallel to each other on one flow surface with the counter electrodes on the opposite flow cell surface. Alternatively, multiple electrodes can be arranged on both surfaces as well. The flow cells used to generate the data in some of the examples described herein have dimensions of 5.8 mm×5.8 mm×100 um.

Figure 21:
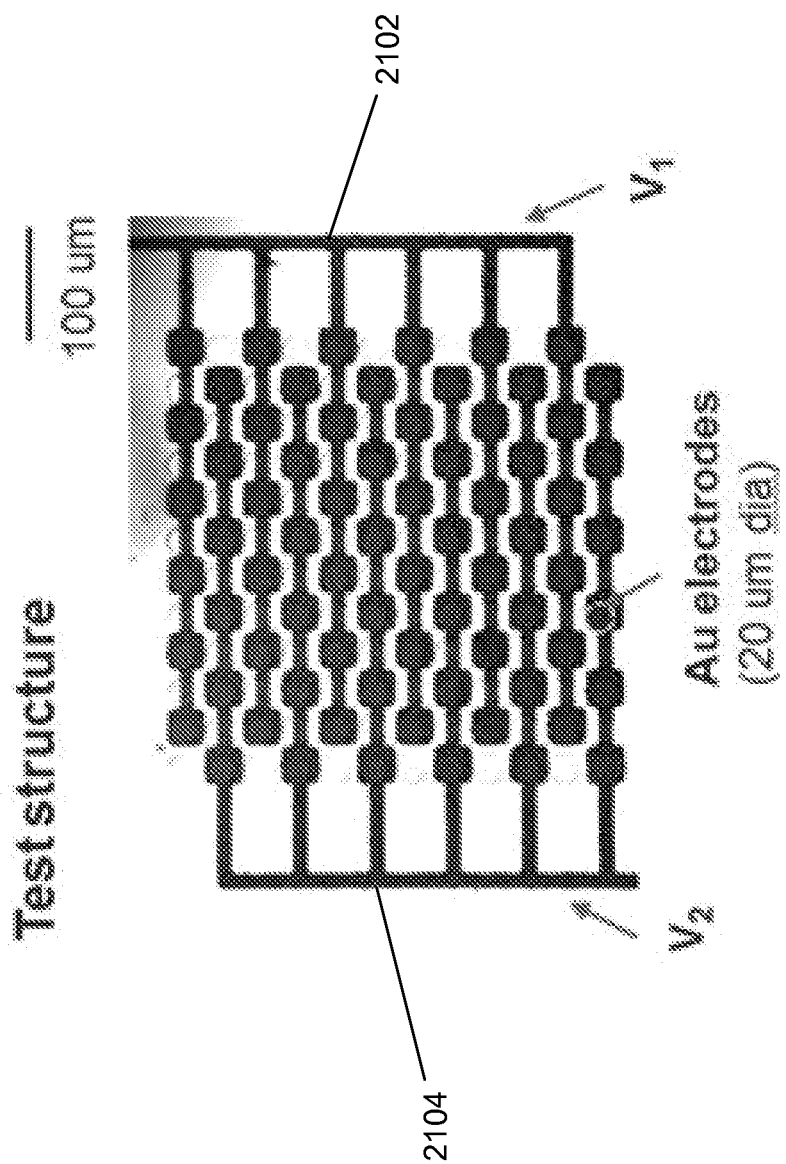
FIG. 21 shows an exemplary configuration of two sets of electrodes controlled by two voltage sources.

FIG. 21 depicts an example of this configuration, where one set of electrodes 2102 was controlled by voltage source V1 and another set of electrodes 2104 was controlled by voltage source V2.

Figure 22:
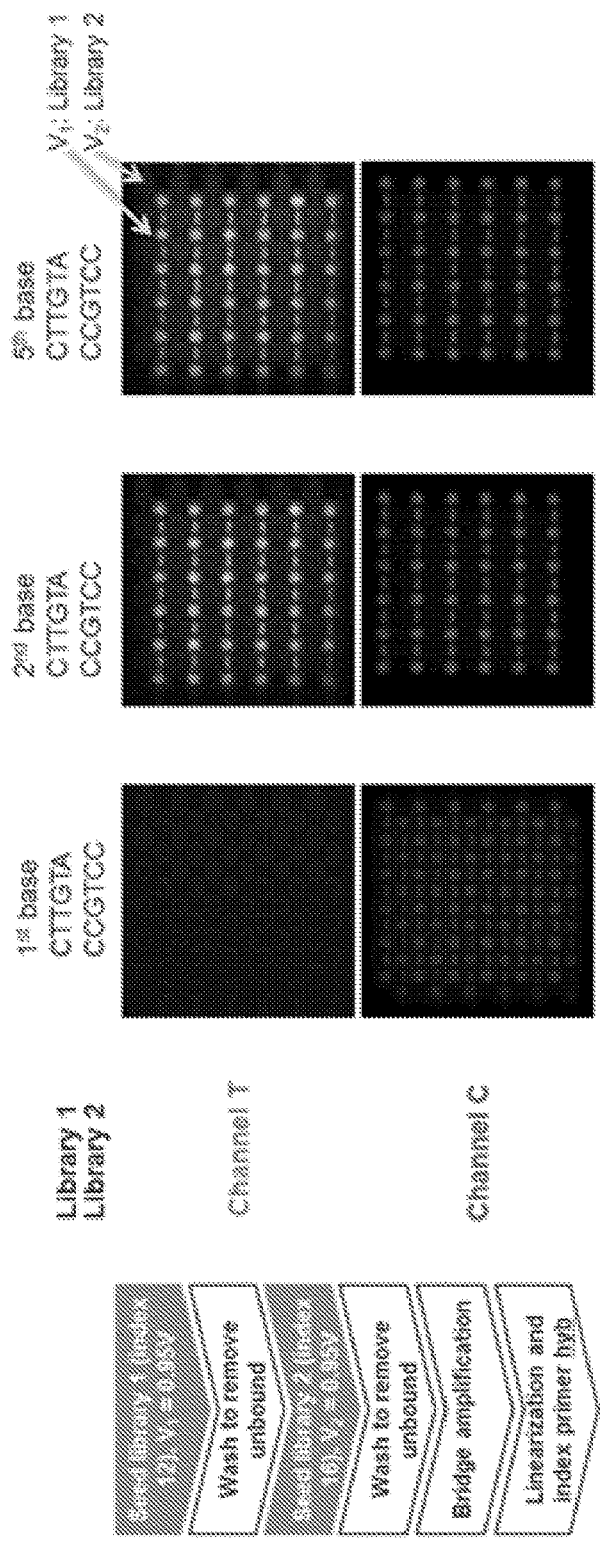
FIG. 22 shows a flow chart of a process of sequentially seeding two libraries while holding the two sets of electrodes at different charges, and the imaging results of the polynucleotide hybridization.

In the example of FIG. 22, two libraries were sequentially loaded onto the library capture surface while activating a different set of electrodes, such that library 1 was localized on the electrodes controlled by V1 and library 2 was localized on the electrodes controlled by V2. After a library was loaded onto the capture surface, the capture surface was washed to remove unbound polynucleotides. After both libraries were loaded, the hybridized polynucleotides underwent bridge amplification and linearization and were subsequently sequenced by synthesis. FIG. 22 demonstrates that subsequent sequencing revealed that the different libraries were localized to different electrodes.

Some embodiments include a method of sequencing a polynucleotide sample, the method comprising:

(a) providing a solid support having a plurality of electrodes disposed thereon, the solid support including a polymer layer over the plurality of electrodes, the polymer layer including a plurality of forward and reverse amplification primers immobilized thereon, the solid support also including electrical leads connected to the plurality of electrodes permitting the electrodes to be independently addressable, the solid support also including a fluid direction system for controllably delivering a plurality of polynucleotide libraries through the solid support at different time periods;

(b) applying a positive charge to a first electrode of the plurality of electrodes;

(c) delivering a first polynucleotide library along the solid support such that polynucleotides from the first polynucleotide library are attracted to forward and reverse amplification primers disposed proximate the first electrode such that members of the first polynucleotide library hybridize to forward and reverse amplification primers proximate the first electrode, wherein members of the first polynucleotide library do not substantially hybridize to forward and reverse amplification primers located proximate electrodes that do not have positive charge applied;

(d) applying a positive charge to a second electrode of the plurality of electrodes; and (e) delivering a second polynucleotide library along the solid support such that polynucleotides from the second polynucleotide library are attracted to forward and reverse amplification primers disposed proximate the second electrode such that members of the second polynucleotide library hybridize to forward and reverse amplification primers proximate the second electrode, wherein members of the second polynucleotide library do not substantially hybridize to forward and reverse amplification primers located proximate electrodes that do not have positive charge applied.

What is claimed is:

1. A flow cell for nucleic acid sequencing, the flow cell comprising:
   (a) a plurality of inlet ports and a plurality of outlet ports,
   (b) a top plate that defines an upper surface of the flow cell and a boundary of the library sequencing region, wherein the top plate is overlaid upon a channel layer, wherein the top plate is coated with a counter electrode;
   (c) the channel layer overlaid upon a bottom plate and defining multiple substantially parallel channels that form a library sequencing region, wherein the multiple substantially parallel channels comprise one to twenty enclosed channels and each of the multiple substantially parallel channels is positioned between one of the plurality of inlet ports and one of the plurality of outlet ports, and wherein each of the multiple substantially parallel channels of the channel layer comprises:
      (i) a library capture surface comprising an inner surface facing a library sequencing region, and
      (ii) a plurality of forward amplification primers having a first sequence and a plurality of reverse amplification primers having a second sequence, wherein both the plurality of forward amplification primers and the plurality of reverse amplification primers are directly immobilized to the inner surface of each of the multiple substantially parallel channels to provide a nucleic acid library capture surface of the library sequencing region; and
   (d) the bottom plate, wherein the bottom plate comprises;
      (i) an inner surface;
      (ii) a plurality of electrodes disposed along the inner surface of the bottom plate and arranged such that each channel of the multiple substantially parallel channels of the channel layer passes over the plurality of electrodes; wherein the plurality of electrodes comprises two to twelve electrodes; each electrode of the plurality of electrodes having a width that spans more than half or all of the width of the channel, or that spans the width of the flow cell, wherein the width of each electrode, the width of the channel, and the width of the flow cell are perpendicular to the direction of flow through the flow cell, wherein the plurality of electrodes comprise at least;
         (a) a first electrode directly under a plurality of forward amplification primers, and a plurality of reverse amplification primers, and (b) a second electrode directly under a plurality of forward amplification primers and a plurality of reverse amplification primers, wherein the first electrode and the second electrode are configured to provide, when charged, an electric field through the library capture surface and into the library sequencing region; and
      (ii) electrical leads connected to the plurality of electrodes to permit each of plurality of electrodes to be independently addressable.

2. The flow cell of claim 1, wherein the top plate comprises a film of transparent electrically conductive film attached to an electrical lead.

3. The flow cell of claim 1, further comprising an attachment layer over the plurality of electrodes to which the plurality of forward amplification primers and the plurality of reverse amplification primers are attached.

4. The flow cell of claim 1, wherein the nucleic acid library capture surface occupies an area of between about 60 $mm^2$ and about 2400 $mm^2$, and wherein polynucleotides are hybridized to the plurality of forward amplification primers and the plurality of reverse amplification primers at a density of 10,000/$mm^2$ to 2,000,000/$mm^2$.

5. The flow cell of claim 1, wherein the plurality of electrodes are disposed in an array.

6. The flow cell of claim 1, wherein the plurality of electrodes are made of a conductor selected from the group consisting of gold, indium-doped tin oxide (ITO), silver, tin, titanium, copper, platinum, palladium, polysilicon, and carbon.

7. The flow cell of claim 3, wherein the plurality of first amplification primers are configured to hybridize to a first gene sequence and are attached to a first region of the flow cell, and wherein the plurality of second amplification primers are configured to hybridize to a second gene sequence and are attached to a second, spatially separate, region of the flow cell.

8. The flow cell of claim 3, wherein the plurality of forward amplification primers and the plurality of reverse amplification primers are disposed on one or more beads immobilized on the attachment layer.

9. The flow cell of claim 1, wherein each channel of the multiple substantially parallel channels passes over at least five electrodes of the plurality of electrodes.

10. The flow cell of claim 1, further comprising fluidic couplings at each inlet port and each outlet port that are configured to deliver a plurality of nucleic acid libraries to the flow cell.

11. The flow cell of claim 1, wherein the width of each electrode of the plurality of electrodes spans the width of the flow cell.

* * * * *

UNITED STATES PATENT AND TRADEMARK OFFICE
CERTIFICATE OF CORRECTION

| | |
|---|---|
| PATENT NO. | : 10,537,889 B2 |
| APPLICATION NO. | : 15/107882 |
| DATED | : January 21, 2020 |
| INVENTOR(S) | : Chenlu Hou et al. |

Page 1 of 1

It is certified that error appears in the above-identified patent and that said Letters Patent is hereby corrected as shown below:

On the Title Page

Column 2 in the Abstract, Line 5, delete "a plurality of a plurality" and insert -- a plurality --, therefor.

In the Claims

In Column 38, Line 31, in Claim 1, delete "(ii)" and insert -- (iii) --, therefor.

Signed and Sealed this
Twenty-eighth Day of April, 2020

Andrei Iancu
*Director of the United States Patent and Trademark Office*